United States Patent
Noguchi et al.

(10) Patent No.: US 7,091,189 B2
(45) Date of Patent: Aug. 15, 2006

(54) MEDICAMENT FOR TREATING LUNG CANCER

(75) Inventors: Toshihiro Noguchi, Ibaraki (JP); Akemi Baba, Oklahoma City, OK (US)

(73) Assignee: Dainippon Sumitomo Pharma Co., Ltd.

( * ) Notice: Subject to any disclaimer, the term of this patent is extended or adjusted under 35 U.S.C. 154(b) by 0 days.

(21) Appl. No.: 10/508,025

(22) PCT Filed: Mar. 17, 2003

(86) PCT No.: PCT/JP03/03206

§ 371 (c)(1),
(2), (4) Date: Sep. 16, 2004

(87) PCT Pub. No.: WO03/077932

PCT Pub. Date: Sep. 25, 2003

(65) Prior Publication Data

US 2005/0119196 A1 Jun. 2, 2005

(30) Foreign Application Priority Data

Mar. 18, 2002 (JP) ............................. 2002-074962

(51) Int. Cl.
*A01N 43/04* (2006.01)
*A01N 43/42* (2006.01)
*A61K 31/70* (2006.01)
*A61K 31/44* (2006.01)

(52) U.S. Cl. ........................... 514/34; 514/27; 514/33; 514/49; 514/283

(58) Field of Classification Search ................ 514/34, 514/27, 33, 49, 283
See application file for complete search history.

(56) References Cited

U.S. PATENT DOCUMENTS

| 6,544,962 B1 * | 4/2003 | Jones et al. ................ 514/49 |
| 6,747,055 B1 * | 6/2004 | Ho et al. ................ 514/425 |
| 2003/0157097 A1 | 8/2003 | Noguchi et al. |
| 2004/0038913 A1 | 2/2004 | Noguchi et al. |

FOREIGN PATENT DOCUMENTS

| WO | WO-02/09754 A1 | 2/2002 |
| WO | WO-02/060453 A1 | 8/2002 |

OTHER PUBLICATIONS

Sumitomo, "Amrubicin Hydrochloride", Drugs of the Future, vol. 22, pp. 1271-1272, 1997.*
Hida et al., Clinical Cancer Research, vol. 6, pp. 2006-2011, 2000.*
Yanagi et al., Japanese Cancer Association, abstract No. 2168, 1989.*
Yamauchi et al., "Combination effects of Amrubicin, a Novel Anthracycline, With Cisplatin on Human Lung Cancer Cells", European Journal of Cancer, vol. 37, suppl. 6, pp. 159, 2001.*
Ettinger, David S., "New Drugs for Chemotherapy-Naive Patients with Extensive-Disease Small Cell Lung Cancer", Seminars in Oncology, (2001), vol. 28, No. 2, Suppl. 4, pp. 27 to 29.
Turrisi, A.T., et al., "The Treatment of Limited Small Cell Lung Cancer: A Report of the Progress Made and Future Prospects", European Journal of Cancer, (2002), vol. 38, Issue 2, pp. 279 to 291.
Fukuoka, M., "Current Perspectives of New Agents in Lung Cancer", Nippon Rinsho (Japanese Journal of Clinical Medicine), (2000), vol. 58, No. 5, pp. 1103 to 1110.
Masuda, N., "Small-Cell Lung Cancer", Nippon Rinsho (Japanese Journal of Clinical Medicine), (2000), vol. 58, No. 5, pp. 1121 to 1126.
Yamauchi, S., et al., "Combination Effects of Amrubicin, A Novel Anthracycline, with Cisplatin on Human Lung Cancer Cells", European Journal of Cancer, (2001), vol. 37, Suppl. 6, p. S46, 159.
Takagi et al., Investigational New Drugs, vol. 14, pp. 357-363, (1996).
Hida et al., Clinical Cancer Research, vol. 6, pp. 2006-2011, (2000).
Ohe et al., Cancer Research, vol. 49, pp. 4098-4102, (Aug. 1, 1989).
Yanagi et al., Abstract of publication in Japanese Cancer Association No. 2168, (1989).
"Amrubicin Hydrocholoride" Drugs of the Future, vol. 22, pp. 1271-1272, (1997), XP009034298.
Takigawa et al., Acta Med Okayama, vol. 46, pp. 249-256, (1992), XP009034562.
Vogl et al., Cancer, vol. 38, pp. 21-26, (1976).

\* cited by examiner

*Primary Examiner*—Shaojia Anna Jiang
*Assistant Examiner*—Traviss McIntosh
(74) *Attorney, Agent, or Firm*—Birch, Stewart, Kolasch & Birch, LLP

(57) ABSTRACT

By using a combination of amrubicin or a pharmaceutically acceptable salt thereof with another medicament for treating lung cancer (irinotecan, vinorelbine, gemcitabine, etc.), it is intended to provide medicaments for treating lung cancer having an improved antitumor therapeutic effect on lung cancer and reduced side effects. Lung cancer can be effectively treated using these medicaments.

16 Claims, 19 Drawing Sheets

MEDICAMENT FOR TREATING LUNG CANCER

TECHNICAL FIELD

The present invention relates to a medicament for treating lung cancer, comprising amrubicin or a pharmaceutically acceptable salt thereof as an active ingredient, for a use in combination with another medicament for treating lung cancer.

BACKGROUND ART

Amrubicin ((+)-(7S,9S)-9-acetyl-9-amino-7-[(2-deoxy-β-D-erythro-pentopyranosyl)oxy]-7,8,9,10-tetrahydro-6,11-dihydroxy-5,12-naphthacenedione) is an anthracycline compound represented by the following chemical structural formula (JP 3-5397B, U.S. Pat. No. 4,673,668):

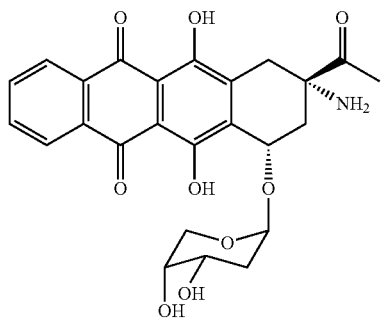

Amrubicin is easily reduced in vivo to form a metabolite (amrubicinol) which is a 13-hydroxylated product. This amrubicinol has a considerably stronger inhibitory activity against growth of tumor cells than that of amrubicin. Doxorubicin and daunomycin, the other anthracycline compounds, also form reduced metabolites, which in contrast have reduced activities (Cancer Chemothr. Pharmacol., 30, 51–57 (1992)). Also for the cardiac toxicity, amrubicin is far weaker than doxorubicin in rabbit chronic experimental model (Invest. New Drug, 15, 219–225 (1997)).

It has been known that, although anthracycline compounds have similar structures, they are different in their indications, action mechanisms and so on as described below. Daunorubicin and idarubicin are approved for treatment of leukemia but are not approved for treatment of solid cancers. On the other hand, doxorubicin, epirubicin, pirarubicin and aclarubicin are approved for treatment of solid cancers. Daunorubicin and doxorubicin inhibit synthesis of DNA and synthesis of RNA in similar degrees but aclarubicin and marcellomycin inhibit synthesis of RNA more strongly than synthesis of DNA; therefore their mechanism of exerting antitumor activities are quite different (JJSHP, 27, 1087–1110 (1991)). It has been known that, in this manner, even if drugs belong to the same category of anthracycline, they have different effect depending on the kind of cancer, and the same anticancer agent has different effect depending on the kind of cancer. Consequently, it is necessary to specifically confirm by experiment whether or not a specific anticancer agent is effective against a specific tumor (cancer).

It has been described that a use of amrubicin hydrochloride in combination with cisplatin or the like exhibits an additive effect on human T-cell leukemia MOLT-3 cell strain and human osteosarcoma MG-63 cell strain (Investigational New Drugs, 14, 357–363 (1996)). Additionally, an effect has been described, in an experiment with murine leukemia P388 cell strain, for a combined use of amrubicin and cisplatin in vivo (Yoshikazu YANAGI et al., Abstracts of publications in Japanese Cancer Association, No. 2168 (1989)). No report, however, has been described for a combined use of amrubicin and another medicament for treating lung cancer against lung cancer and for side effects.

DISCLOSURE OF INVENTION

The problem to be solved by the present invention is to provide a medicament for treating lung cancer with increasing antitumor therapeutic effect and reducing side effects.

As the result of extensive studies, the present inventors have found the facts that lung cancers can be remarkably cured without increasing side effects observed in the single use of agents when amrubicin and another medicament for treating lung cancer are used in combination, and that the side effects can be dramatically reduced when respective doses are decreased keeping the therapeutic effect in the combined use of amrubicin and another medicament for treating lung cancer. Furthermore, the present inventors have also found that the expression level of carbonyl reductase 1 gene, which product can convert amrubicin into its active metabolite amrubicinol, is higher in the cells of lung cancer such as small cell lung cancer, lung adenocarcinoma, squamous cell lung carcinoma and large cell lung carcinoma than in normal lung cells and leukemic cells. Accordingly, they have found that amrubicin is selectively changed into amrubicinol and works in the cells of lung cancer more than in normal lung cells or leukemic cells, and thus the side effects will be reduced by the present invention.

The present invention has been completed according to the above knowledge.

Namely, the present invention is as follows:

[1] A medicament for treating lung cancer, comprising amrubicin or a pharmaceutically acceptable salt thereof as an active ingredient, for a use in combination with another medicament for treating lung cancer.

[2] The medicament for treating lung cancer as described in [1], wherein the lung cancer is small cell lung cancer, lung adenocarcinoma, squamous cell lung carcinoma or large cell lung carcinoma.

[3] The medicament for treating lung cancer as described in [1], wherein the lung cancer is small cell lung cancer or squamous cell lung carcinoma.

[4] The medicament for treating lung cancer as described in any of [1] to [3], wherein the amrubicin or a pharmaceutically acceptable salt thereof is amrubicin hydrochloride.

[5] The medicament for treating lung cancer as described in any of [1] to [4], wherein the other medicament for treating lung cancer is irinotecan, nogitecan, vinorelbine, vincristine, gemcitabine, 5-FU, paclitaxel, docetaxel or ZD 1839.

[6] The medicament for treating lung cancer as described in any of [1] to [4], wherein the other medicament for treating lung cancer is irinotecan, vinorelbine, gemcitabine, paclitaxel, docetaxel or ZD 1839.

[7] The medicament for treating lung cancer as described in any of [1] to [6], which is administered simultaneously with, separately from or sequentially with the other medicament for treating lung cancer.

[8] The medicament for treating lung cancer as described in any of [1] to [7], for a patient carrying a lung cancer to which the other medicament for treating lung cancer has been administered or is planned to be administered.

[9] The medicament for treating lung cancer as described in any of [1] to [8], which is packaged such that about 60 to about 150 mg/m$^2$ of amrubicin or a pharmaceutically acceptable salt thereof is administered in a single dose or in 2 to 5 divided doses.

[10] The medicament for treating lung cancer as described in [9], which is packaged such that about 80 to about 130 mg/m$^2$ of amrubicin or a pharmaceutically acceptable salt thereof is administered in a single dose.

[11] The medicament for treating lung cancer as described in [9], which is packaged such that about 110 to about 130 mg/m$^2$ of amrubicin or a pharmaceutically acceptable salt thereof is administered in a single dose.

[12] The medicament for treating lung cancer as described in [9], which is packaged such that about 25 to about 50 Mg/m$^2$ of amrubicin or a pharmaceutically acceptable salt thereof is administered once a day for 3 days.

[13] The medicament for treating lung cancer as described in [9], which is packaged such that about 30 to about 45 mg/m$^2$ of amrubicin or a pharmaceutically acceptable salt thereof is administered once a day for 3 days.

[14] The medicament for treating lung cancer as described in [9], which is packaged such that about 35 to about 45 mg/m$^2$ of amrubicin or a pharmaceutically acceptable salt thereof is administered once a day for 3 days.

[15] The medicament for treating lung cancer as described in any of [12] to [14], wherein amrubicin or a pharmaceutically acceptable salt thereof is administered for continuous 3 days.

[16] The medicament for treating lung cancer as described in any of [1] to [15], wherein the other medicament for treating lung cancer is administered in a combined use of about 0.4 times to about 1.0 time of the maximum tolerated dose or 0.4 times to about 1.0 time of the maximum administered dose.

[17] The medicament for treating lung cancer as described in any of [1] to [16], for a patient having a lung cancer, wherein the patient is one having failed to continue receiving the treatment with the other medicament for treating lung cancer because of side effects, and wherein the patient is receiving administration of said other medicament in an amount that will cause reduced side effect.

[18] A use of amrubicin or a pharmaceutically acceptable salt thereof for the manufacture of a medicament for treating lung cancer for a use in combination with another medicament for treating lung cancer.

[19] A method for treating a lung cancer which comprises administering amrubicin or a pharmaceutically acceptable salt thereof and another medicament for treating lung cancer.

The medicament for treating lung cancer of the invention is a medicament for treating lung cancer comprising amrubicin or a pharmaceutically acceptable salt thereof as an active ingredient and is used in combination with another medicament for treating lung cancer.

Amrubicin or pharmaceutically acceptable salts thereof can be prepared, for example, according to J. Org. Chem., 52, 4477–4485 (1987). The pharmaceutically acceptable salts of amrubicin include acid addition salts and base addition salts. The acid addition salts include, for example, inorganic acid salts such as hydrochloride, hydrobromide, sulfate, hydroiodide, nitrate, phosphate and the like; and organic acid salts such as citrate, oxalate, acetate, formate, propionate, benzoate, trifluoroacetate, fumarate, maleate, tartrate, aspartate, glutamate, methanesulfonate, benzenesulfonate, camphorsulfonate and the like. The base addition salts include, for example, inorganic base addition salts such as sodium salt, potassium salt, calcium salt, magnesium salt, ammonium salt and the like; and organic base addition salts such as triethylammonium salt, triethanolammonium salt, pyridinium salt, diisopropylammonium salt and the like. Preferred pharmaceutically acceptable salts include hydrochloride and the like.

The maximum tolerated dose of amrubicin or pharmaceutically acceptable salts thereof is, referring to amrubicin hydrochloride, 25 mg/kg (75 mg/m$^2$) for mice and 130 mg/m$^2$ for humans in once a day single dose, and 50 mg/m$^2$ per day for administration in 3 continuous days.

Another medicament for treating lung cancer is any medicament for treating lung cancer except amrubicin and pharmaceutically acceptable salts, for example, it includes DNA topoisomerase I inhibitors (e.g. irinotecan, nogitecan), tublin polymerization inhibitors (e.g. vinorelbine, vincristine), antimetabolites (e.g. gemcitabine, 5-FU), tublin depolymerization inhibitors (e.g. paclitaxel, docetaxel) and tyrosine kinase inhibitors (e.g. ZD 1839).

Preferable is described below, for example, for the other medicament for treating lung cancer.

Irinotecan: JP 60-19790A, U.S. Pat. No. 4,604,463, J. Clin. Oncol., 11, 909(1993)

Nogitecan: EP 0321122B1

Vinorelbine: JP 55-31096A, U.S. Pat. No. 4,307,100, Cancer Letters, 27, 285 (1985)

Vincristine

Gemcitabine: U.S. Pat. No. 4,808,614, Cancer Treat. Rev., 19, 45–55 (1993) 5-FU (5-Fluorourasil)

Paclitaxel: J. Am. Chem. Soc., 93, 2325–2327 (1971)

Docetaxel: J. Natl. Cancer Inst., 83, 288–291 (1991) ZD 1839 (4-(3-chloro-4-fluoroanilino)-7-methoxy-6-(3-morpholinopropoxy)quinazoline; generic name Gefitinib; Product name IRESSA): Drugs 2000: 60 Suppl. 1, 33~40

The maximum tolerated dose of irinotecan is 120 mg/kg for mice and the maximum administered dose for humans is, for example, 150 mg/m$^2$ at intervals of a week and 350 mg/m$^2$ at intervals of 3 weeks. The maximum tolerated dose of vinorelbine is 16 mg/kg for mice and the maximum administered dose for humans is 25 mg/m$^2$. The maximum tolerated dose of gemcitabine is 300 mg/kg/dose for mice and the maximum administered dose for humans is 1000 mg/m$^2$. The maximum tolerated dose of paclitaxel is 12.5 mg/kg/dose for mice and the maximum administered dose for humans is 210 mg/m$^2$ The maximum tolerated dose of docetaxel is 30 mg/kg/dose for mice and the maximum administered dose for humans is 70 mg/m$^2$. The maximum tolerated dose of ZD 1839 is 200 mg/kg for mice and 700 mg/day for humans, and the maximum administered dose for humans is about 500 mg/day.

The lung cancer includes, for example, small cell lung cancer, lung adenocarcinoma, squamous cell lung carcinoma, large cell lung carcinoma, carcinoids, adenoid cystic carcinoma, mucoepidermoid carcinoma, malignant mixed tumor and the like. Among them, examples in which the medicament for treating lung cancer of the invention exhibit preferred effect include small cell lung cancer, lung adenocarcinoma, squamous cell lung carcinoma, large cell lung carcinoma and the like, and particularly preferred one is small cell lung cancer and squamous cell lung carcinoma.

From results of Examples 1 to 3 with mice, the following facts are found:

(1) In a combined use of 0.5 times (12.5 mg/kg) of the maximum tolerated dose of amrubicin hydrochloride and 0.5 times of the maximum tolerated dose of the other medicament for treating lung cancer, an anticancer effect was observed at a similar level as compared with those found in groups in which the maximum tolerated dose of each of respective agents was administered alone. On the other hand, their side effects were significantly decreased.

(2) In a combined use of 0.8 times or 1.0 time (20 or 25 mg/kg) of the maximum tolerated dose of amrubicin hydrochloride and 0.8 times or 1.0 time of the maximum tolerated dose of the other medicament for treating lung cancer, a stronger anticancer effect was observed as compared with those found in groups to which the maximum tolerated dose of each of respective agents was administered alone. On the other hand, their side effects were not increased but at a similar level.

As described above, by the combined use of about 0.5 to about 1 time of the maximum tolerated dose of amrubicin or a pharmaceutically acceptable salt thereof and about 0.5 to about 1 time of the maximum tolerated dose of the other medicament for treating lung cancer, anticancer effect can be obtained safely and sufficiently without increasing side effects of said medicament for treating lung cancer and amrubicin or pharmaceutically acceptable salts thereof or sometimes decreasing the side effects. For example, when the side effects of said medicament for treating lung cancer or amrubicin are taken up as a problem, a lower dose within the range of about 0.5 to about 1 time of the maximum tolerated dose of amrubicin or a pharmaceutically acceptable salt thereof and about 0.5 to about 1 time of the maximum tolerated dose of the other medicament for treating, lung cancer can be applied; on the other hand, when the side effects of said medicament for treating lung cancer or amrubicin are not taken up as a problem, a higher dose within a range of about 0.5 to about 1 time of the maximum tolerated dose of amrubicin or a pharmaceutically acceptable salt thereof and about 0.5 to about 1 time of the maximum tolerated dose of said medicament for treating lung cancer can be used for safely obtaining the maximum anticancer effect.

In the treatment of human lung cancers, while the amount may be suitably varied depending on conditions, age, body weight and so on of the patient, for example, about 60 to about 150 mg/m$^2$ of amrubicin or a pharmaceutically acceptable salt thereof and 0.4 to 1.0 time of the maximum tolerated dose (or maximum administered dose) of the other medicament for treating lung cancer can be used in combination. Amrubicin or a pharmaceutically acceptable salt thereof can be administered, for example, in an amount of about 60 to about 150 mg/m$^2$ in a single dose or in 2 to 5 divided doses. Preferred schedule for administration of amrubicin or a pharmaceutically acceptable salt thereof includes, for example, a single administration, once daily administration for 3 days and the like, and includes most preferably once daily administration over 3 continuous days. The dose for a single administration includes, for example, a range of about 80 to about 130 mg/m$^2$, and includes preferably about 110 mg/m$^2$ to about 130 mg/m$^2$ and more preferably about 120 mg/m$^2$. The dose per day for administration over 3 continuous days includes, for example, a range of about 25 to about 50 mg/m$^2$, preferably a range of about 30 to about 45 mg/m$^2$, more preferably a range of about 35 to about 45 mg/m$^2$, and most preferably about 40 mg/m$^2$, about 45 mg/m$^2$ and the like.

The amount of administration of the other medicament for treating lung cancer to be administered in combination includes, for example, a range of about 0.4 to about 1.0 time of the maximum tolerated dose or maximum administered dose in a single dose, preferably about 0.5 to about 0.9 times of the maximum tolerated dose or maximum administered dose in a single dose. For example, it is about 75 to about 135 mg/m$^2$ for irinotecan, about 12.5 to about 22.5 mg/m$^2$ for vinorelbine, about 500 to about 900 mg/m$^2$ for gemcitabine, about 105 to about 190 mg/m$^2$ for paclitaxel, about 35 to about 63 mg/m$^2$ for docetaxel and about 350 to about 630 mg/day for ZD 1839. With regard to ZD 1839, it is known that a rather lower dosage gives effect, thus it is possible to provide the effect in combination even in about 125 to about 630 mg/day. In addition, the other medicament for treating lung cancer can be administered in several divided doses, within a day or over several days.

In patients carrying a lung cancer treated with the other medicament for treating lung cancer, when it has been judged that the treatment can not be continued because of side effects of said medicament, a treatment with decreased side effects of said medicament for treating lung cancer can be continued by an administration of said medicament for treating lung cancer in a dose with reduced side effects and additional administration of amrubicin or a pharmaceutically acceptable salt thereof. The dose of said medicament for treating lung cancer for reduction of side effects includes, for example, a range of about 0.4 to about 0.8 times of the maximum tolerated dose (or maximum administered dose) and preferably includes a range of about 0.4 to about 0.6 times of the maximum tolerated dose (or maximum administered dose).

In the medicament for treating lung cancer of the invention, amrubicin or a pharmaceutically acceptable salt thereof is administered simultaneously with, separately from or sequentially with the other medicament for treating lung cancer. When it is administered separately or sequentially, amrubicin or a pharmaceutically acceptable salt thereof may be administered before or be administered after the other medicament for treating lung cancer. The interval of both administration can suitably be set and may be, for example, 1 to several hours, ten to several tens hours, 1 to several days, 1 week and the like. For example, it is preferred, in view of patient's convenience such as visiting hospital or the like, that amrubicin or a pharmaceutically acceptable salt thereof and the other medicament for treating lung cancer are administered on the same day.

While the administration of the medicament for treating lung cancer of the invention suitably varies depending on conditions, age and body weight of patient, form for administration, amount for administration of the other medicament for treating lung cancer to be administered in combination, frequency of administration and the like, it is preferred that the both administrations are repeated after the administration of the above amrubicin or a pharmaceutically acceptable salt thereof and that of the other medicament for treating lung cancer at an interval of about 7 days to about 60 days. Most preferably, repetition is made at an interval of about 2 weeks to about 4 weeks and further preferably at an interval of about 3 weeks.

Amrubicin or a pharmaceutically acceptable salt thereof can usually be administered parenterally (for example, intravenous, intraarterial, subcutaneous or intramuscular injection; intravesically, intraperitoneally, intrapleurally, topically, rectally, percutaneously, nasally and so on). Preferred route includes intravenous injection. In addition, oral administration is also possible, and forms for oral administration include tablets, capsules, pills, granules, powders, solutions, syrups, suspensions and the like.

The other medicament for treating lung cancer can usually be administered parenterally (for example, intravenous, intraarterial, subcutaneous or intramuscular injection; intravesically, intraperitoneally, intrapleurally, topically, rectally, percutaneously, nasally and so on). Preferred route includes intravenous injection. In addition, oral administration is also possible, and forms for oral administration include tablets, capsules, pills, granules, powders, solutions, syrups, suspensions and the like.

In the medicament for treating lung cancer of the invention, further the other anticancer agent, irradiation therapy, surgical measures and the like can further be combined. Additionally, it can be in the form of a kit for combined medicament for treating lung cancer comprising (a) a first composition comprising amrubicin or a pharmaceutically acceptable salt thereof as an active ingredient and (b) a second composition comprising another medicament for treating lung cancer as an active ingredient.

EXAMPLES

The invention is described below in more detail with reference to Examples, which do not limit the invention.

Example 1

Antitumor Activity by a Combination of Amrubicin Hydrochloride and Irinotecan:

Human small cell lung cancer LX-1 cell strain was subcutaneously transplanted to nude mice (59 animals) at 6 weeks of age. After 11 days from the tumor transplantation, 36 animals having a tumor volume of about 100 to 300 mm$^3$ were allotted to 6 groups consisting of 6 animals per group. On the same day, the animals received intravenous administration, respectively, of cysteine buffer for "vehicle group", the maximum tolerated dose of amrubicin hydrochloride (25 mg/kg) for "an amrubicin hydrochloride alone administration group", the maximum tolerated dose of irinotecan (120 mg/kg) for "irinotecan alone administration group", 0.5 times of the maximum tolerated dose of amrubicin hydrochloride and 0.5 times of the maximum tolerated dose of irinotecan for "combined administration group (0.5×MTD) ", 0.8 times of the maximum tolerated dose of amrubicin hydrochloride and 0.8 times of the maximum tolerated dose of irinotecan for "combined administration group (0.8× MTD)", the maximum tolerated dose of amrubicin hydrochloride and the maximum tolerated dose of irinotecan for "combined administration group (1×MTD)". Thereafter, tumor volume and body weight of the mice were measured for 23 days.

Amrubicin hydrochloride was dissolved in a cysteine buffer (containing 0.4 mg/ml L-cysteine hydrochloride monohydrate and 6.25 mg/ml lactose) to give a solution of 2.5 mg/ml, which was diluted with a cysteine buffer to give solutions of 2.0 and 1.25 mg/ml. Each 10 ml/kg aliquot of the solutions was administered as the maximum tolerated dose, the 0.8 times dose or the 0.5 times dose of amrubicin hydrochloride.

Irinotecan was administered by giving 120, 96 or 60 mg/kg aliquot of Topotecin Injection (containing 20 mg/ml), purchased from Daiichi Pharmaceutical Co., Ltd., as the maximum tolerated dose, the 0.8 times dose or the 0.5 times dose of irinotecan.

FIGS. 1 and 2 show changes in tumor volume and body weight for the combined administration (0.5×MTD) group together with data for the amrubicin hydrochloride alone administration group and those for the irinotecan alone administration group.

FIGS. 3 and 4 show changes in tumor volume and body weight for the combined administration (0.8×MTD) group together with data for the amrubicin hydrochloride independent administration group and those for the irinotecan independent administration group.

FIGS. 5 and 6 show changes in tumor volume and body weight for the combined administration (1×MTD) group together with data for the amrubicin hydrochloride alone administration group and those for the irinotecan alone administration group.

TABLE 1 shows the minimum T/C % of tumor growth rate in respective groups. The minimum T/C % was calculated as follows:

Minimum T/C %: the minimum value of ratio (%) of tumor growth rate[*] for respective administration groups to tumor growth rate[*] for the vehicle administration group within the period for measurement.

[*]Tumor growth rate: a ratio of an average value of tumor volume for a group of 6 animals at respective point in time of measurement to an average value of tumor volume for a group of 6 animals at respective point in time of drug administration.

TABLE 1

| Administration | Minimum T/C(%) Average ± SD |
|---|---|
| Amrubicin hydrochloride 25 mg/kg | 40.79 ± 5.92 |
| Irinotecan 120 mg/kg | 45.61 ± 12.94 |
| Amrubicin hydrochloride 25 mg/kg + Irinotecan 120 mg/kg | 24.24 ± 5.48 |
| Amrubicin hydrochloride 20 mg/kg + Irinotecan 96 mg/kg | 28.17 ± 3.85 |
| Amrubicin hydrochloride 12.5 mg/kg + Irinotecan 60 mg/kg | 45.05 ± 4.74 |

1. Results in the Combined Administration (0.5×MTD) Group:

As shown in FIG. 1, the antitumor effect in the combined administration was a similar effect as compared with those in the maximum tolerated dose administration groups for respective single agents. Thus, the minimum T/C % was 40.79% in the amrubicin hydrochloride alone administration group, 45.61% in the irinotecan alone administration group and 45.05% in the combined administration (0.5×MTD) group.

The side effects as evaluated by loss in the body weight of animals, as shown in FIG. 2, was at a similar degree to those in the irinotecan alone administration group as compared with the single administration groups for respective single agents.

2. Results in the Combined Administration (0.8×MTD) Group:

As shown in FIG. 3, there was a reduction of tumor, and the antitumor effect in the combined administration was a stronger antitumor effect as compared with those in the single administration groups for respective single agents. Thus, the minimum T/C % was 40.79% in the amrubicin hydrochloride alone administration group, 45.61% in the irinotecan alone administration group and 28.17% in the combined administration (0.8×MTD) group.

The side effects as evaluated by loss in the body weight of animals, as shown in FIG. 4, was at a similar degree to those in the amrubicin hydrochloride alone administration group.

3. Results in the Combined Administration (1×MTD) Group:

As shown in FIG. 5, there was a reduction of tumor as in the case of 0.8 times administration, and the antitumor effect in the combined administration was a stronger antitumor effect as compared with those in the single administration groups for respective single agents. Thus, the minimum T/C % was 40.79% in the amrubicin hydrochloride alone administration group, 45.61% in the irinotecan alone administration group and 24.24% in the combined administration (1×MTD) group.

For the side effects as evaluated by loss in the body weight of animals, as shown in FIG. 6, there was a transitory loss in the body weight by about 3 g, but the weight recovered.

Example 2

Antitumor Activity by a Combination of Amrubicin Hydrochloride and Vinorelbine:

Antitumor activity by a combination of amrubicin hydrochloride and vinorelbine was tested in the same way as Example 1, except that human squamous cell lung carcinoma QC-56 cell strain was used in place of human small cell lung cancer LX-1 cell strain and that the maximum tolerated dose of vinorelbine was set at 16 mg/kg. Vinorelbine was administered by giving 16, 12.8 or 8 ml/kg aliquot of Navelbine Injection (containing 10 mg/ml), purchased from Kyowa Hakko Kogyo Co., Ltd., as the maximum tolerated dose, the 0.8 times dose or the 0.5 times dose of vinorelbine. In addition, nude mice (100 animals) at 5 weeks of age were used.

FIGS. 7 and 8 show changes in tumor volume and body weight for the combined administration (0.5×MTD) group together with data for the amrubicin hydrochloride alone administration group and those for the vinorelbine alone administration group.

FIGS. 9 and 10 show changes in tumor volume and body weight for the combined administration (0.8×MTD) group together with data for the amrubicin hydrochloride independent administration group and those for the vinorelbine independent administration group.

FIGS. 11 and 12 show changes in tumor volume and body weight for the combined administration (1×MTD) group together with data for the amrubicin hydrochloride alone administration group and those for the vinorelbine alone administration group.

TABLE 2 shows the minimum T/C % of tumor growth rate in respective groups.

TABLE 2

| Administration | Minimum T/C(%) Average ± SD |
|---|---|
| Amrubicin hydrochloride 25 mg/kg | 37.73 ± 7.56 |
| Vinorelbine 16 mg/kg | 38.24 ± 12.87 |
| Amrubicin hydrochloride 25 mg/kg + Vinorelbine 16 mg/kg | 27.15 ± 8.14 |
| Amrubicin hydrochloride 20 mg/kg + Vinorelbine 12.8 mg/kg | 31.10 ± 13.48 |
| Amrubicin hydrochloride 12.5 mg/kg + Vinorelbine 8 mg/kg | 42.43 ± 20.08 |

1. Results in the Combined Administration (0.5×MTD) Group:

As shown in FIG. 7, the antitumor effect in the combined administration was a similar effect as compared with those in the maximum tolerated dose administration groups for respective single agents. Thus, the minimum T/C % was 37.73% in the amrubicin hydrochloride alone administration group, 38.24% in the vinorelbine alone administration group and 42.43% in the combined administration (0.5×MTD) group.

For the side effects as evaluated by loss in the body weight of animals, as shown in FIG. 8, the increase of the side effect was not observed because of rare loss in the body weight compared with the single administration groups for respective single agents.

2. Results in the Combined Administration (0.8×MTD) Group:

As shown in FIG. 9, there was a reduction of tumor, and the antitumor effect in the combined administration was a stronger antitumor effect as compared with those in the single administration groups for respective single agents. Thus, the minimum T/C % was 37.73% in the amrubicin hydrochloride alone administration group, 38.24% in the vinorelbine alone administration group and 31.10% in the combined administration (0.8×MTD) group.

The side effects as evaluated by loss in the body weight of animals, as shown in FIG. 10, was at a similar degree to those in the single administration groups for respective single agents.

3. Results in the Combined Administration (1×MTD) Group:

As shown in FIG. 11, there was a reduction of tumor as in the case of 0.8 times administration, and the antitumor effect in the combined administration was a stronger antitumor effect as compared with those in the single administration groups for respective single agents. Thus, the minimum T/C % was 37.73% in the amrubicin hydrochloride alone administration group, 38.24% in the vinorelbine alone administration group and 27.15% in the combined administration (1×MTD) group.

For the side effects as evaluated by loss in the body weight of animals, as shown in FIG. 12, there was a transitory loss in the bodyweight by about 1.4 g, but the weight recovered.

Example 3

Antitumor Activity by a Combination of Amrubicin Hydrochloride and Gemcitabine:

Antitumor activity by a combination of amrubicin hydrochloride and gemcitabine was tested in the same way as Example 2, except that the maximum tolerated dose of gemcitabine was set at 300 mg/kg/day and the administration was intraperitoneally once per week in two cycles. Gemcitabine was administered by giving 300, 240 or 150 ml/kg aliquot of Gemzar Injection (containing 200 mg/bial), purchased from Eli Lilly Japan K.K., as the maximum tolerated dose, the 0.8 times dose or the 0.5 times dose of gemcitabine. In addition, nude mice (80 animals) at 5 weeks of age were used.

FIGS. 13 and 14 show changes in tumor volume and body weight for the combined administration (0.5×MTD) group together with data for the amrubicin hydrochloride alone administration group and those for the gemcitabine alone administration group.

FIGS. 15 and 16 show changes in tumor volume and body weight for the combined administration (0.8×MTD) group together with data for the amrubicin hydrochloride independent administration group and those for the gemcitabine independent administration group.

FIGS. 17 and 18 show changes in tumor volume and body weight for the combined administration (1×MTD) group together with data for the amrubicin hydrochloride alone administration group and those for the gemcitabine alone administration group.

TABLE 3 shows the minimum T/C % of tumor growth rate in respective groups.

TABLE 3

| Administration | Minimum T/C(%) Average ± SD |
|---|---|
| Amrubicin hydrochloride 25 mg/kg | 51.06 ± 16.56 |
| Gemcitabine 300 mg/kg i.p. 2q7d | 69.47 ± 26.06 |
| Amrubicin hydrochloride 25 mg/kg + Gemcitabine 300 mg/kg | 41.33 ± 15.12 |
| Amrubicin hydrochloride 20 mg/kg + Gemcitabine 240 mg/kg | 34.27 ± 14.05 |
| Amrubicin hydrochloride 12.5 mg/kg + Gemcitabine 150 mg/kg | 56.67 ± 18.87 |

1. Results in the Combined Administration (0.5×MTD) Group:

As shown in FIG. 13, the antitumor effect in the combined administration was a similar effect as compared with those in the maximum tolerated dose administration groups for respective single agents. Thus, the minimum T/C % was 51.06% in the amrubicin hydrochloride alone administration group, 69.47% in the gemcitabine alone administration group and 56.67% in the combined administration (0.5× MTD) group.

For the side effects as evaluated by loss in the body weight of animals, as shown in FIG. 14, a remarkable reducing effect of the side effects, possibly caused by halving the dose of gemcitabine, was observed as compared with the single administration groups for respective single agents.

2. Results in the Combined Administration (0.8×MTD) Group:

As shown in FIG. 15, there was a reduction of tumor, and the antitumor effect in the combined administration was a stronger antitumor effect as compared with those in the single administration groups for respective single agents. Thus, the minimum T/C % was 51.06% in the amrubicin hydrochloride alone administration group, 69.47% in the gemcitabine alone administration group and 34.27% in the combined administration (0.8×MTD) group.

The side effects as evaluated by loss in the body weight of animals, as shown in FIG. 16, was at a similar degree to those in the amrubicin hydrochloride alone administration group.

3. Results in the Combined Administration (1×MTD) Group:

As shown in FIG. 17, there was a reduction of tumor as in the case of 0.8 times administration, and the antitumor effect in the combined administration was a stronger antitumor effect as compared with those in the single administration groups for respective single agents. Thus, the minimum T/C % was 51.06% in the amrubicin hydrochloride alone administration group, 69.47% in the gemcitabine alone administration group and 41.33% in the combined administration (1×MTD) group.

The side effects as evaluated by loss in the body weight of animals, as shown in FIG. 18, was at a similar degree to those in the gemcitabine alone administration group.

As described in the above Examples 1 to 3, side effects were reduced and remarkable therapeutic effects were observed in the combined administration of amrubicin hydrochloride with irinotecan, vinorelbine and gemcitabine. In addition, as it can be understood from FIGS. 1 to 18, the effects by the combined use appear with particular significance during 2 weeks from the administration and the effects almost disappear after 3 weeks. Consequently, it is preferred that the administration be repeated again after about 2 weeks to about 4 weeks, and particularly, re-administration is carried out after about 3 weeks and continued thereafter.

With regard to paclitaxel (the maximum tolerated dose, 12.5 mg/kg/dose), the effects by the combined use with amrubicin hydrochloride can be confirmed similar to Example 1. Further, with regard to ZD 1839 (the maximum tolerated dose, 200 mg/kg), the effects by the combined use with amrubicin hydrochloride can be confirmed by carrying out the similar test to Example 1 provided that human squamous cell carcinoma A431 cell strain was used.

Example 4

In Vitro Combination Effects of Amrubicinol Hydrochloride with Irinotecan:

The in vitro combination effects of amrubicinol hydrochloride with irinotecan hydrochloride were examined by using human non-small cell lung cancer cell.

Human non-small cell lung cancer cell strain A549 was obtained from ATCC (American Type Culture Collection). In a medium comprising D-MEM (Dulbecco's Modified Eagle Medium) and 10% bovine fetal serum (FCS), human non-small cell lung cancer cell strain A549 was subcultured. The culture was carried out in a incubator with 5% $CO_2$ at 37° C. The same medium was also used in the following experiments.

Test agents were prepared as below.

Irinotecan hydrochloride was obtained from Daiichi Pharmaceutical Co., Ltd. and provided after 2 fold serial dilutions with medium in use.

Amrubicinol was prepared by a method described in a literature (Ishizumi et al., J. Org. Chem., 52, 4477–4485 (1987)). Amrubicinol hydrochloride maintained in a deep freezer (−80° C.) was measured each of about 1 mg, kept in a freezer (−20° C.), and then dissolved in distilled water to give 1 mg/ml in use, which was used after sterilization by filtration followed by 2 fold serial dilution with the medium.

Human non-small cell lung cancer cell strain A549 on subculture was subjected to a trypsin treatment, suspended in the medium and seeded on a 96-well plate. The seeding density was set to be $5 \times 10^2$ cells/0.1 ml/well. After seeding, cells were cultured overnight in an incubator with 5% $CO_2$ at 37° C. (Day 0).

To the group for evaluating a single agent, were added 0.05 ml/well of a diluted solution of a test agent and 0.05 ml/well of the medium; and to the group for evaluating the combination effect, were added 0.05 ml/well of a diluted solution of amrubicinol hydrochloride and a diluted solution of 0.05 ml/well of irinotecan hydrochloride (Day 1). The experiments were conducted with n=3 for the agent-treated group, and with n=6 for the untreated (control) group.

Until Day 4, culture was conducted in an incubator with 5% $CO_2$ at 37° C.

On Day 4, 0.02 ml of WST solution (a solution containing 1.3 mg/ml WST-1 (2-(4-Iodophenyl)-3-(4-nitrophenyl)-5-(2,4-disulfophenyl)-2H-tetrazolium, sodium salt) and 0.14 mg/ml 1-Methoxy PMS (1-Methoxy-5-methylphenazinium methyl sulfate) in a phosphate buffer solution (PBS)) was added to each of the wells. Thereafter, culture was conducted in an incubator with 5% $CO_2$ at 37° C. for 2–4 hours. Absorbance of the culture was then measured with MICROPLATE READER Model 3550-UV (BioRad), and living cell number was measured.

Growth rate f was determined by the following formula:

f=(mean value of absorbance at each of the agent concentrations)/(mean value of absorbance at the agent concentration of 0 mg/ml)

Absorbance: $A_{420}-A_{630}$ log((1/f)−1) was plotted versus log(agent concentration), and then a regression line was drawn in accordance with a least square method to find the slope m and X intercept. Exp(X intercept value) represents $IC_{50}$ value (concentration of the agent required for 50% inhibition of the cell growth). While the ratio of the concentrations of amrubicinol hydrochloride and irinotecan hydrochloride is 1:25, m and $IC_{50}$ value were obtained respectively. (Hereinafter, $IC_{50}$ value is represented as $D_m$, and amrubicinol hydrochloride is represented with the subscript 1 while irinotecan hydrochloride is represented with the subscript 2. e.g.: $D_{m1}$)

Concentration D of amrubicinol hydrochloride and irinotecan hydrochloride required for achieving a particular inhibition rate of growth (fa) was determined by the formula ①. The concentration for the single agent was defined as $Df_1$ and $Df_2$, while the concentration when used in combination was defined as $Dx_1$ and $Dx_2$, and thus a Combination Index (CI) was calculated by the formula ② (M. Pegram et al., Oncogene, 18, 2241–2251 (1999)).

$$D=D_m \times \{fa/(1-fa)\}^{1/m} \qquad ①$$

$$CI=Dx_1/Df_1+Dx_2/Df_2+(Dx_1 \times Dx_2)/(Df_1 \times Df_2) \qquad ②$$

Evaluation is made as an additive effect at CI=1, as a synergistic effect at CI<1, and as an antagonistic effect at CI>1.

FIG. 19 shows in vitro combination effects of amrubicinol hydrochloride with irinotecan hydrochloride, in which a horizontal axis represents an inhibition rate of growth fa and a vertical axis represents Combination Index (CI). As shown in FIG. 19, the Combination Index (CI) indicated a lower value of 1 at the range of fa=0.1 to 0.9. Thus, in the combination of amrubicinol hydrochloride with irinotecan hydrochloride, a large synergistic effect was revealed according to the determination of the combination effect by CI.

Example 5

Fluctuation Analysis for Expression of Carbonyl Reductase Gene in Normal and Tumor Tissues:

DNA chip analysis was conducted using total RNAs prepared with 69 samples from human lung normal tissue, and 44 samples from lung adenocarcinoma, 32 samples from squamous cell lung carcinoma, 5 samples from large cell lung carcinoma and 18 samples from leukemia cell. The DNA chip analysis was carried out with Gene Chip Human Genome U95A, B, C, D and E from Affymetrix. Specifically, the analysis was performed with a procedure consisting of (1) preparation of a cDNA from a total RNA, (2) preparation of a labeled cRNA from said cDNA, (3) fragmentation of the labeled cRNA, (4) hybridization of the fragmented cRNA with a probe array, (5) staining of the probe array, (6) scanning of the probe array and (7) analysis of gene expression.

(1) Preparation of a cDNA from a Total RNA:

Each of 11 μl of mixed solutions containing 10 μg of each of total RNAs prepared with 69 samples from human lung normal tissue, and 44 samples from lung adenocarcinoma, 32 samples from squamous cell lung carcinoma, 5 samples from large cell lung carcinoma and 18 samples from leukemia cell and 100 pmols of T7–(dT)24 primer (manufactured by Amersham) was heated at 70° C. for 10 minutes and cooled on ice. After cooling, 4 μl of 5× First Strand cDNA Buffer contained in SuperScript Choice System for cDNA Synthesis (manufactured by Gibco-BRL), 2 μl of 0.1 M DTT (dithiothreitol) contained in said kit and 1 μl of 10 mM dNTP Mix were added and the mixture was heated at 42° C. for 2 minutes. Further, 2 μl (400 U) of SuperScript II RT contained in said kit was added. The mixture was heated at 42° C. for 1 hour and cooled on ice. After cooling, 91 μl of DEPC treated water (manufactured by Nacalai Tesque, Inc.), 30 μl of 5× Second Strand Reaction Buffer contained in said kit, 3 μl of 10 mM dNTP Mix, 1 μl (10 U) of E. coli DNA Ligase contained in said kit, 4 μl (40 U) of E. coli DNA Polymerase I contained in said kit and 1 μl (2 U) of E. coli RNAaseH contained in said kit were added and reacted at 16° C. for 2 hours. Then, after adding 2 μl (10 U) of T4 DNA Polymerase contained in said kit and reacting at 16° C. for 5 minutes, 10 μl of 0.5 M EDTA was added. Then, 162 μl of phenol/chloroform/isoamyl alcohol solution (manufactured by Nippongene) was added and mixed. The mixed solution was transferred to Phase Lock Gel Light (manufactured by Eppendorf), which was previously centrifuged at room temperature and 14,000 rpm for 30 seconds, centrifuged at room temperature and 14,000 rpm for 2 minutes and 145 μl of aqueous layer was transferred to an Eppendorf tube. To the obtained solution were added 72.5 μl of 7.5 M ammonium acetate solution and 362.5 μl of ethanol, and after mixing, the mixture was centrifuged at 4° C. and 14,000 rpm for 20 minutes. After centrifugation, the supernatant was discarded to give a DNA pellet containing the prepared cDNA. Then, 0.5 ml of 80% ethanol was added to said pellet and the mixture was centrifuged at 4° C. and 14,000 rpm for 5 minutes. The supernatant was discarded. After repeating again the same treatment, the pellet was dried and dissolved in 12 μl of DEPC treated water.

By the above procedure, cDNAs were obtained from total RNAs derived from 69 samples from human lung normal tissue, and 44 samples from lung adenocarcinoma, 32 samples from squamous cell lung carcinoma, 5 samples from large cell lung carcinoma and 18 samples from leukemia cell.

(2) Preparation of a Labeled cRNA from Said cDNA:

To 5 μl of each of the cDNA solutions prepared in the above (1) were mixed 17 μl of DEPC treated water, 4 μl of 10×HY Reaction Buffer contained in BioArray High Yield RNA Transcript Labeling Kit (manufactured by ENZO), 4 μl of 10× Biotin Labeled Ribonucleotides contained in said kit, 4 μl of 10×DTT contained in said kit, 4 μl of 10× RNase Inhibitor Mix contained in said kit and 2 μl of 20×T7 RNA Polymerase contained in said kit, and reacted at 37° C. for 5 hours. After the reaction, 60 μl of DEPC treated water was added to the reaction solution and the prepared labeled cRNAs were purified with RNeasy Mini Kit according to the attached protocol.

(3) Fragmentation of the Labeled cRNA:

To a solution containing 20 μg of each of labeled cRNAs purified in the above (3) were added 8 μl of 5× Fragmentation Buffer (200 mM tris-acetate, pH 8.1 (manufactured by Sigma), 500 mM potassium acetate (manufactured by Sigma) and 150 mM magnesium acetate (manufactured by Sigma)). After heating 40 µl of the obtained reaction solution at 94° C. for 35 minutes, the solution was placed in ice. This allowed fragmentation of the labeled cRNAs.

(4) Hybridization of the Fragmented cRNA with a Probe Array:

To 40 µl of each of the fragmented cRNAs obtained in the above (3) were mixed 4 µl of 5 nM Control Oligo B2 (manufactured by Amersham), 4 µl of 100× Control cRNA Cocktail, 40 µg of Herring sperm DNA (manufactured by Promenga), 200 µg of Acetylated BSA (manufactured by Gibco-BRL), 200 µl of 2×MES Hybridization Buffer (200 mM MES, 2 M [Na$^+$], 40 mM EDTA, 0.02% Tween 20 (manufactured by Pierce), pH 6.5–6.7) and 144 µl of DEPC treated water to give 400 µl hybridized cocktail. Each of the obtained hybridized cocktails was heated at 99° C. for 5 minutes, and additionally at 45° C. for 5 minutes. After heating, the cocktail was centrifuged at room temperature and 14,000 rpm for 5 minutes to give a supernatant of the hybridized cocktail.

On the other hand, after rotating Human genome U95 probe array (manufactured by Affymetrix) filled with 1×MES hybridization buffer in a hybridization oven at 45° C. and 60 rpm for 10 minutes, 1×MES hybridization buffer was removed to give a probe array. To the probe array was added 200 µl of the supernatant of the hybridized cocktail obtained above, and the mixture was rotated in a hybridization oven at 45° C. and 60 rpm for 16 hours to give a probe array hybridized with fragmented cRNA.

(5) Staining of the Probe Array:

After collecting and removing the hybridized cocktail from each of the already hybridized probe array obtained in the above (4), the product was filled with Non-Stringent Wash Buffer (6×SSPE (prepared by diluting 20×SSPE (manufactured by Nacalai Tesque)), 0.01% Tween 20 and 0.005% Antifoam 0-30 (manufactured by Sigma)). Then, the fragmented cRNA and hybridized probe array were placed in respective positions of GeneChip Fluidics Station 400 (manufactured by Affymetrix) set with Non-Stringent Wash Buffer and Stringent Wash Buffer (100 mM MES, 0.1 M NaCl and 0.01% Tween 20). Then according to the staining protocol EuKGE-WS2, staining was carried out with a first staining solution (10 µg/ml Streptavidin Phycoerythrin (SAPE) (manufactured by Molecular Probe), 2 mg/ml Acetylated BSA, 100 mM MES, 1 M NaCl (manufactured by Ambion), 0.05% Tween 20 and 0.005% Antifoam 0-30) and a second staining solution (100 µg/ml Goat IgG (manufactured by Sigma), 3 µg/ml Biotinylated Anti-Streptavidin antibody (manufactured by Vector Laboratories), 2 mg/ml Acetylated BSA, 100 mM MES, 1 M NaCl, 0.05% Tween 20 and 0.005% Antifoam 0-30).

(6) Scanning of the Probe Array and (7) Analysis of Gene Expression:

Each of probe arrays stained in the above (5) was subjected to HP GeneArray Scanner (manufactured by Affymetrix) to read the staining pattern.

Expression of carbonyl reductase 1 gene on the probe array was analyzed with GeneChip Workstation System (manufactured by Affymetrix) based on the staining pattern. Then, normalization and comparative analysis of gene expression were preformed according to the analysis protocol.

As the result, in human leukemia cells, it was found that the expression frequency of carbonyl reductase 1 was 11% (2 cases in 18 cases) and median of expression level was −39, indicating that the gene is hardly expressed. On the other hand, in human lung tissues, it was found that the expression frequency of carbonyl reductase 1 was 55% (24 cases in 44 cases), 63% (20 cases in 32 cases), 40% (2 cases in 5 cases) and 32% (22 cases in 69 cases) in adenocarcinoma, squamous cell carcinoma, large cell carcinoma and normal tissue, respectively, and expression level was 51, 96, 34 and 22, respectively, indicating that the expression of carbonyl reductase 1 was enhanced in lung cancer tissues as compared with the lung normal tissue and, particularly, the expression levels in lung adenocarcinoma and squamous cell carcinoma were more than 2 times and 4 times that in lung normal tissue, respectively.

INDUSTRIAL APPLICABILITY

Figure 1:
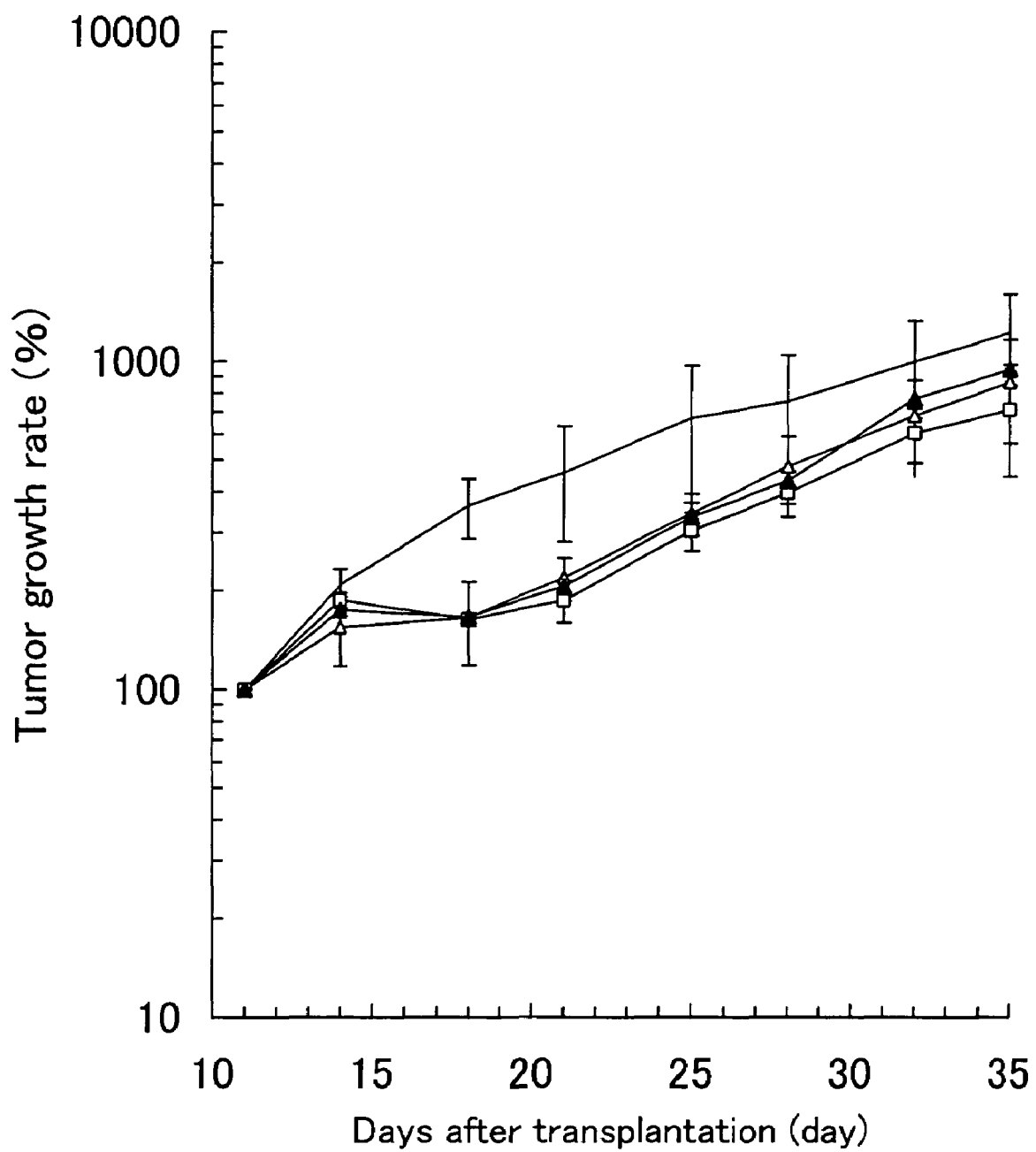
FIG. 1 shows an inhibitory effect of growth of small cell lung cancer cell when 0.5 times of the maximum tolerated dose (MTD) of amrubicin hydrochloride and 0.5 times of the maximum tolerated dose of irinotecan are used in combination. Line denotes a vehicle group, □ denotes an amrubicin hydrochloride alone administration group, ∆ denotes an irinotecan alone administration group and ▲ denotes a combined administration group.
Figure 2:
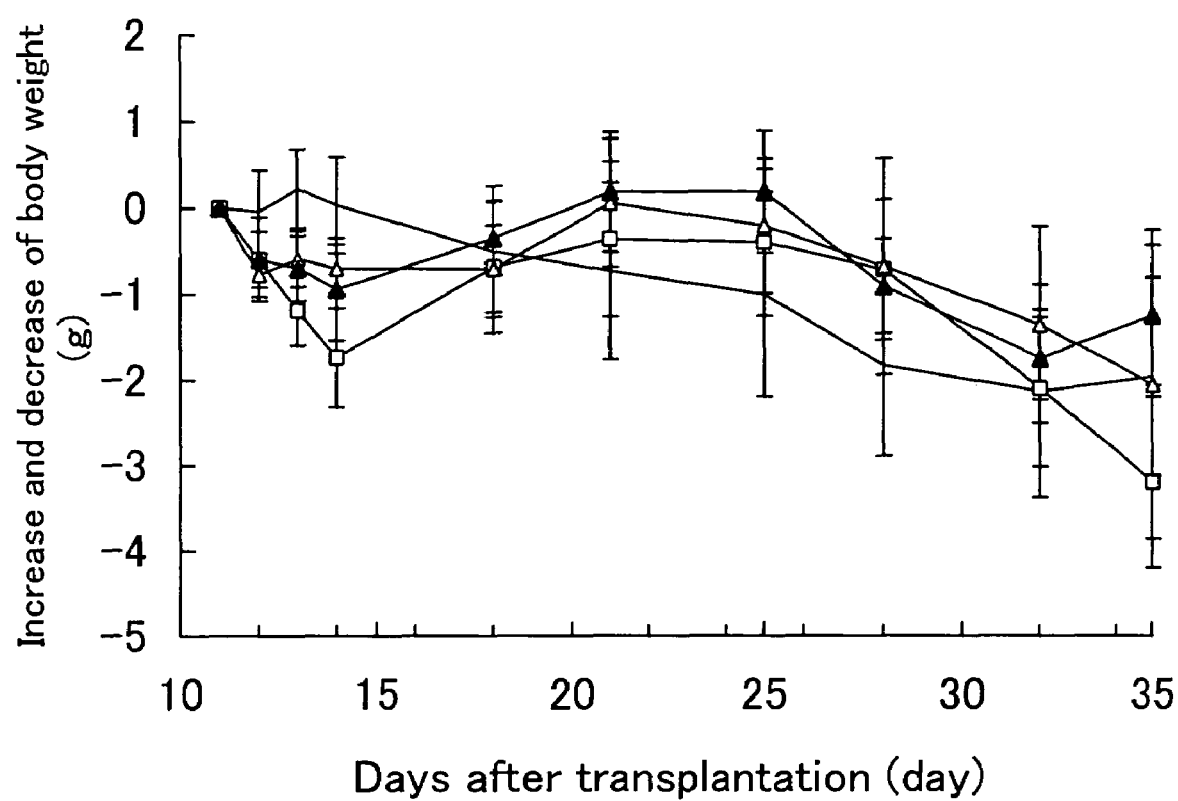
FIG. 2 shows a reducing effect of the body weight as a side effect when 0.5 times of the maximum tolerated dose of amrubicin hydrochloride and 0.5 times of the maximum tolerated dose of irinotecan are used in combination. Line denotes a vehicle group, □ denotes an amrubicin hydrochloride alone administration group, ∆ denotes an irinotecan alone administration group and ▲ denotes a combined administration group.
Figure 3:
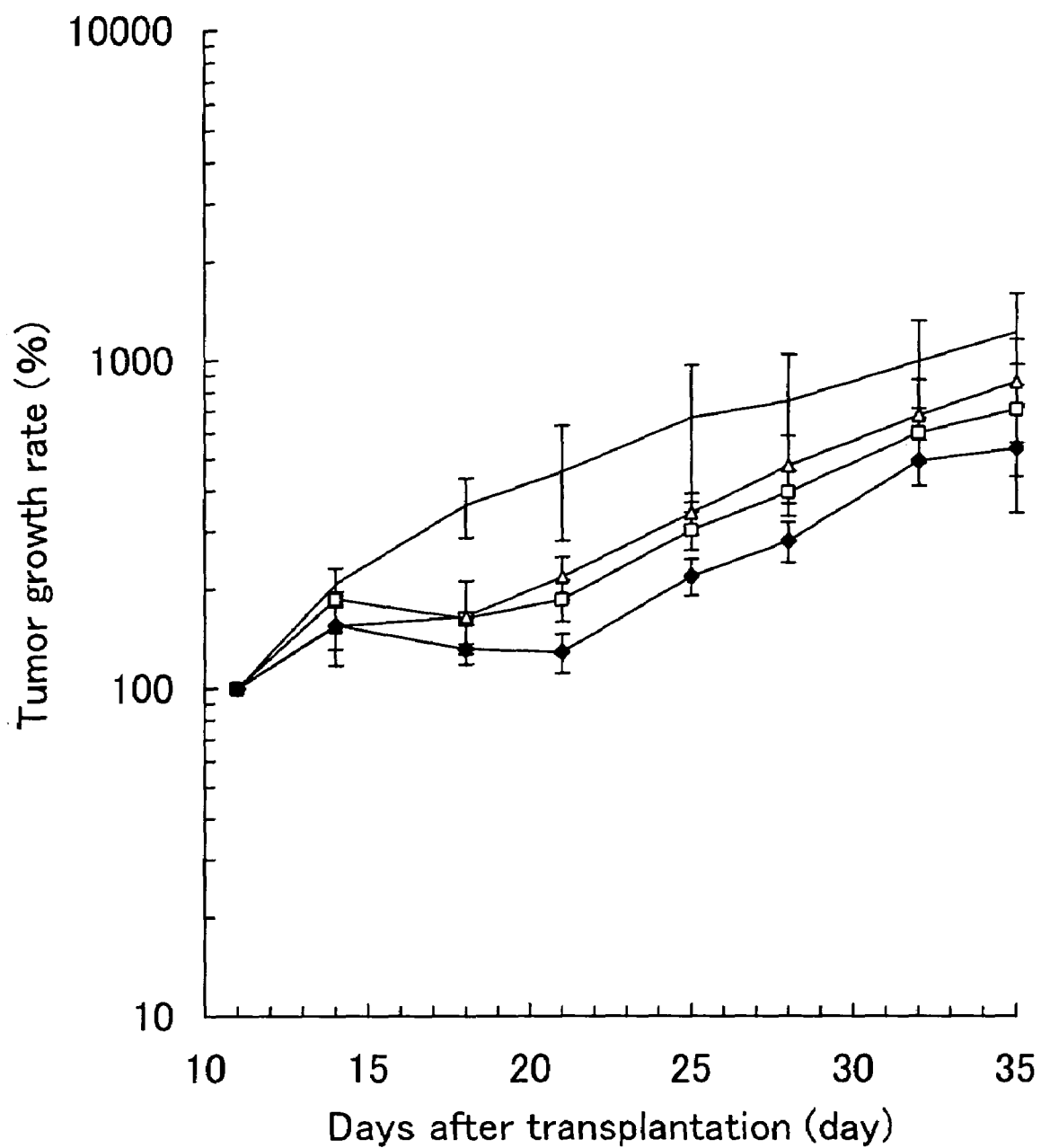
FIG. 3 shows an inhibitory effect of growth of small cell lung cancer cell when 0.8 times of the maximum tolerated dose of amrubicin hydrochloride and 0.8 times of the maximum tolerated dose of irinotecan are used in combination. Line denotes a vehicle group, □ denotes an amrubicin hydrochloride alone administration group, ∆ denotes an irinotecan alone administration group and ♦ denotes a combined administration group.
Figure 4:
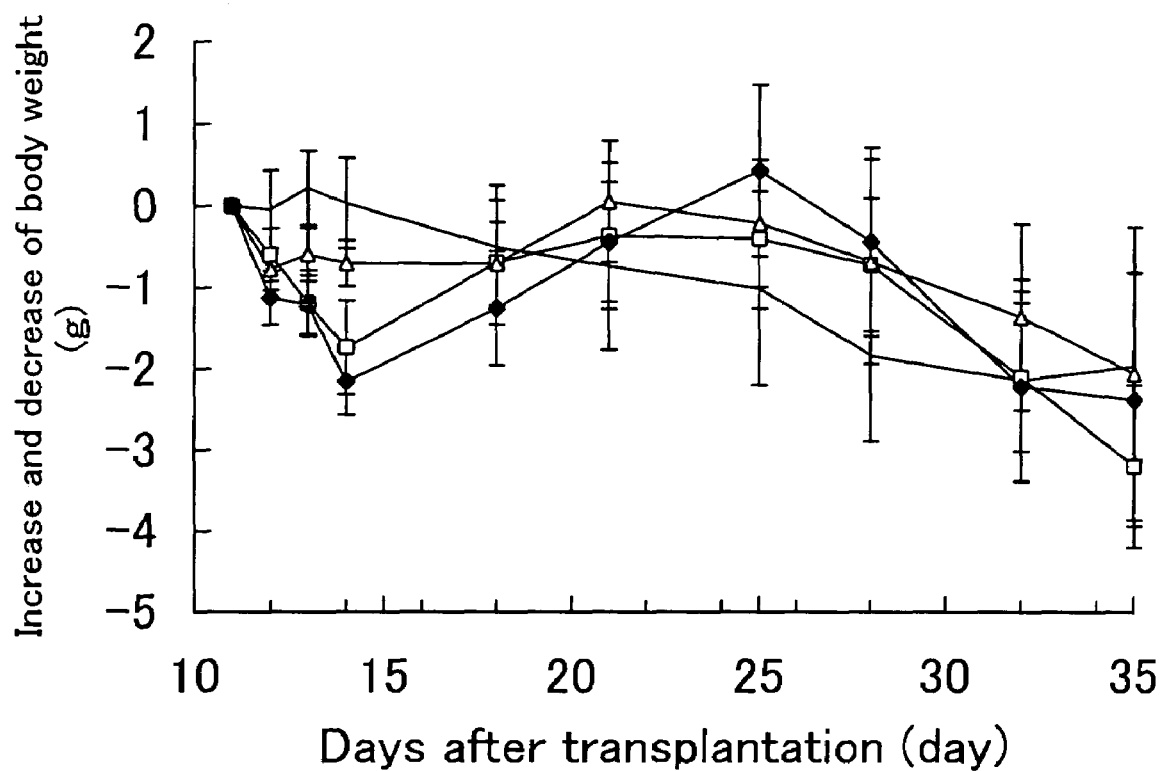
FIG. 4 shows a reducing effect of the body weight as a side effect when 0.8 times of the maximum tolerated dose of amrubicin hydrochloride and 0.8 times of the maximum tolerated dose of irinotecan are used in combination. Line denotes a vehicle group, □ denotes an amrubicin hydrochloride alone administration group, ∆ denotes an irinotecan alone administration group and ♦ denotes a combined administration group.
Figure 5:
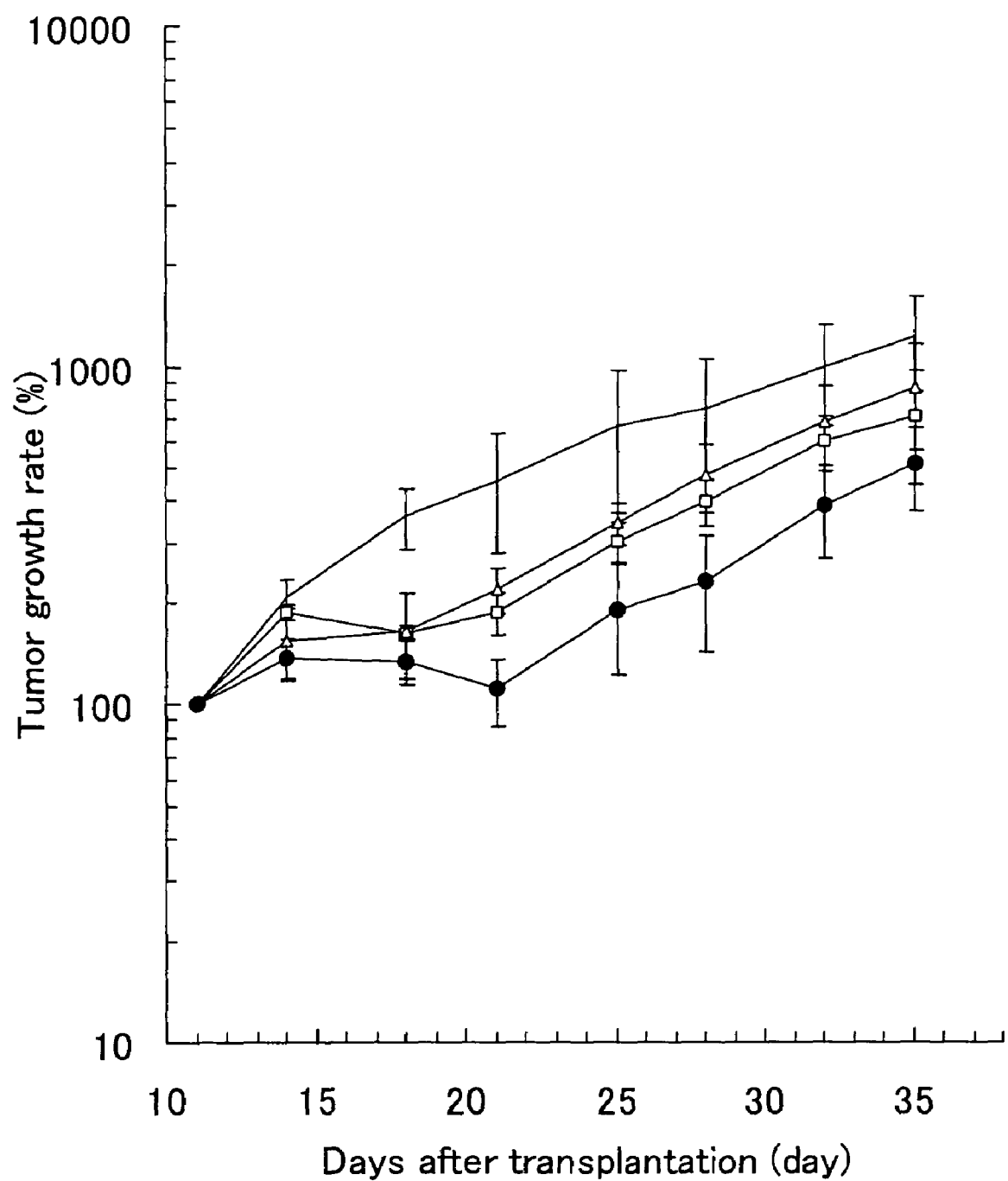
FIG. 5 shows an inhibitory effect of growth of small cell lung cancer cell when 1.0 time of the maximum tolerated dose of amrubicin hydrochloride and 1.0 time of the maximum tolerated dose of irinotecan are used in combination. Line denotes a vehicle group, □ denotes an amrubicin hydrochloride alone administration group, ∆ denotes an irinotecan alone administration group and ● denotes a combined administration group.
Figure 6:
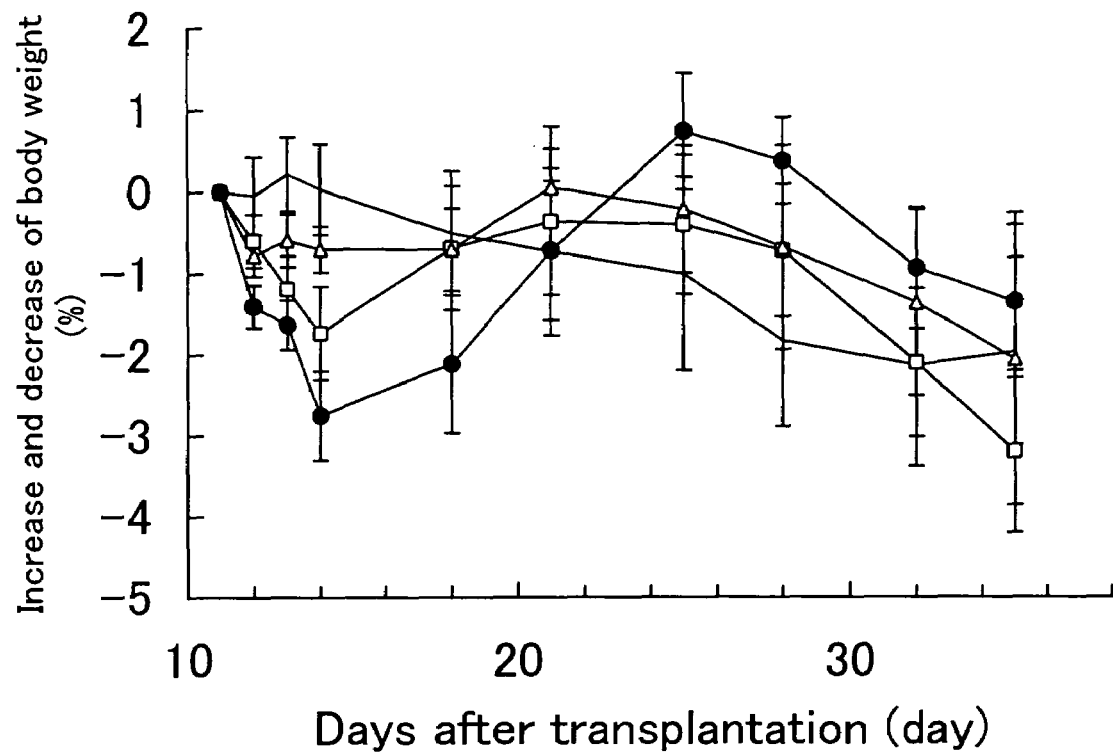
FIG. 6 shows a reducing effect of the body weight as a side effect when 1.0 time of the maximum tolerated dose of amrubicin hydrochloride and 1.0 time of the maximum tolerated dose of irinotecan are used in combination. Line denotes a vehicle group, □ denotes an amrubicin hydrochloride alone administration group, ∆ denotes an irinotecan alone administration group and ● denotes a combined administration group.
Figure 7:
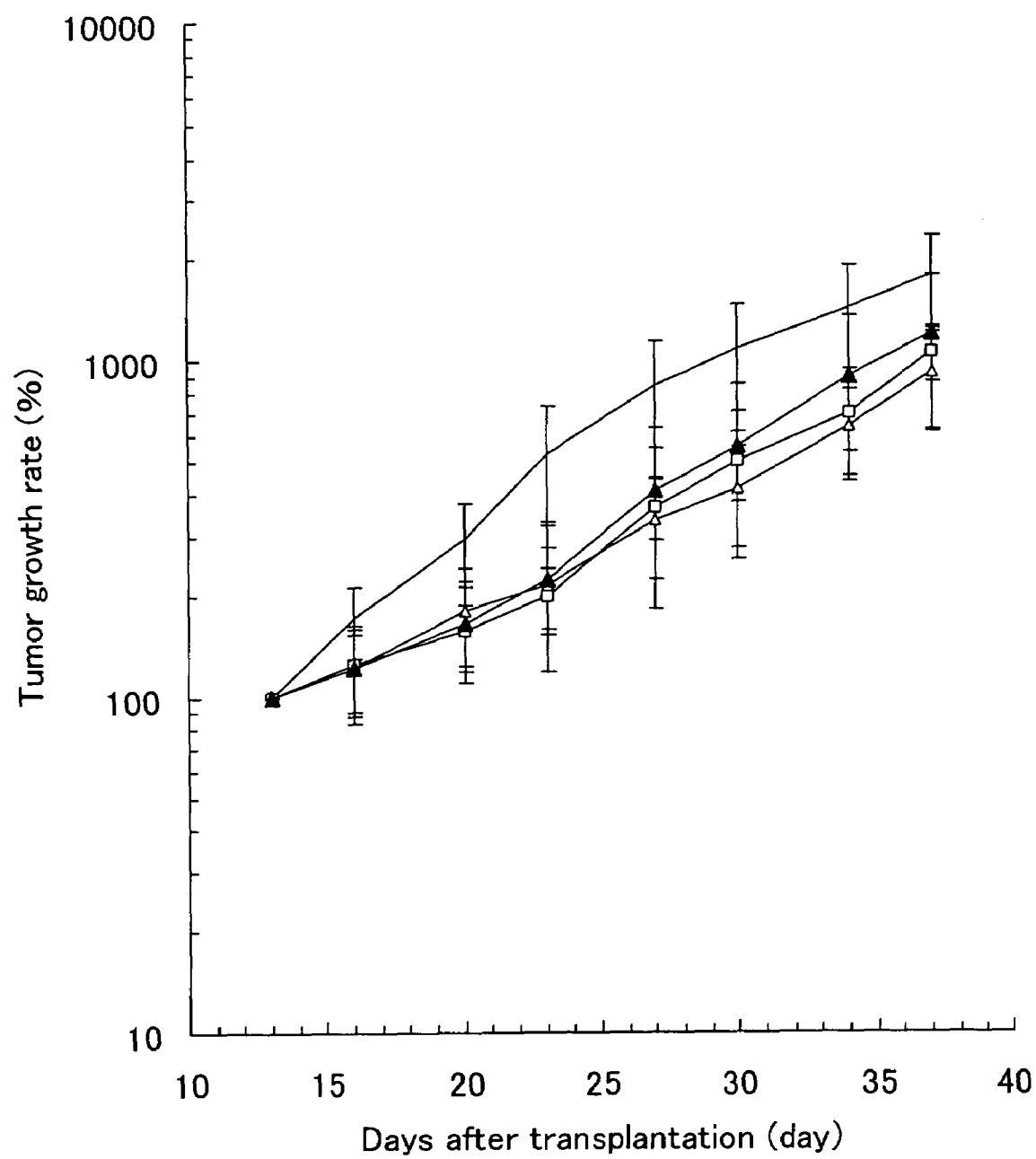
FIG. 7 shows an inhibitory effect of growth of squamous cell lung carcinoma cell when 0.5 times of the maximum tolerated dose of amrubicin hydrochloride and 0.5 times of the maximum tolerated dose of vinorelbine are used in combination. Line denotes a vehicle group, □ denotes an amrubicin hydrochloride alone administration group, Δ denotes a vinorelbine alone administration group and ▲ denotes a combined administration group.
Figure 8:
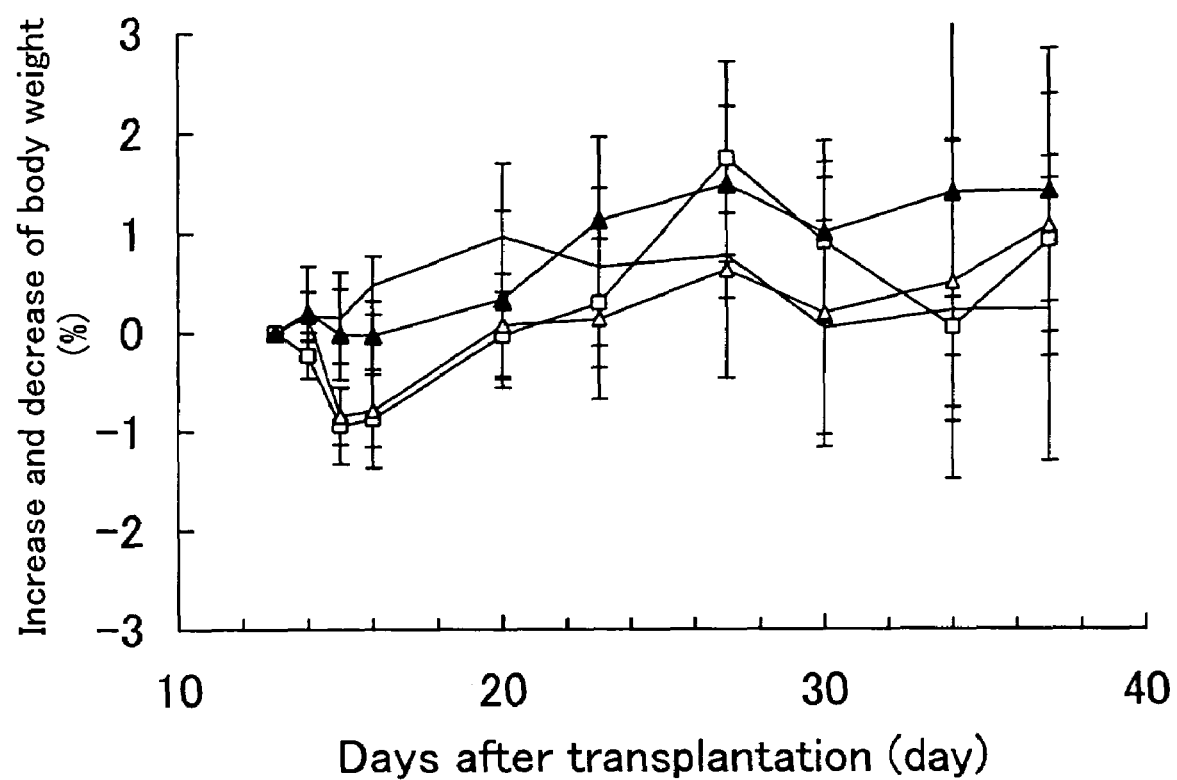
FIG. 8 shows a reducing effect of the body weight as a side effect when 0.5 times of the maximum tolerated dose of amrubicin hydrochloride and 0.5 times of the maximum tolerated dose of vinorelbine are used in combination. Line denotes a vehicle group, □ denotes an amrubicin hydrochloride alone administration group, Δ denotes a vinorelbine alone administration group and ▲ denotes a combined administration group.
Figure 9:
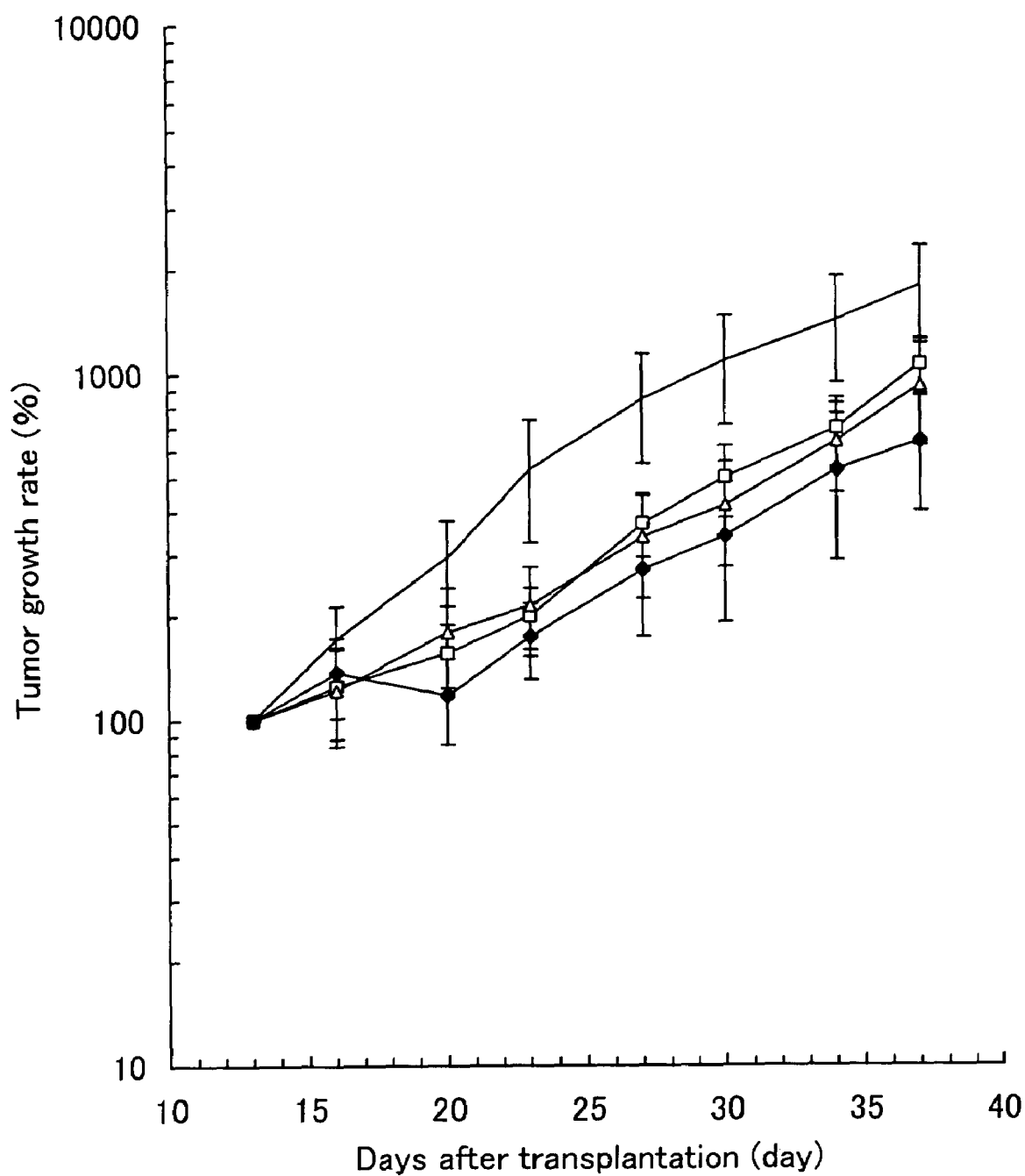
FIG. 9 shows an inhibitory effect of growth of squamous cell lung carcinoma cell when 0.8 times of the maximum tolerated dose of amrubicin hydrochloride and 0.8 times of the maximum tolerated dose of vinorelbine are used in combination. Line denotes a vehicle group, □ denotes an amrubicin hydrochloride alone administration group, Δ denotes a vinorelbine alone administration group and ♦ denotes a combined administration group.
Figure 10:
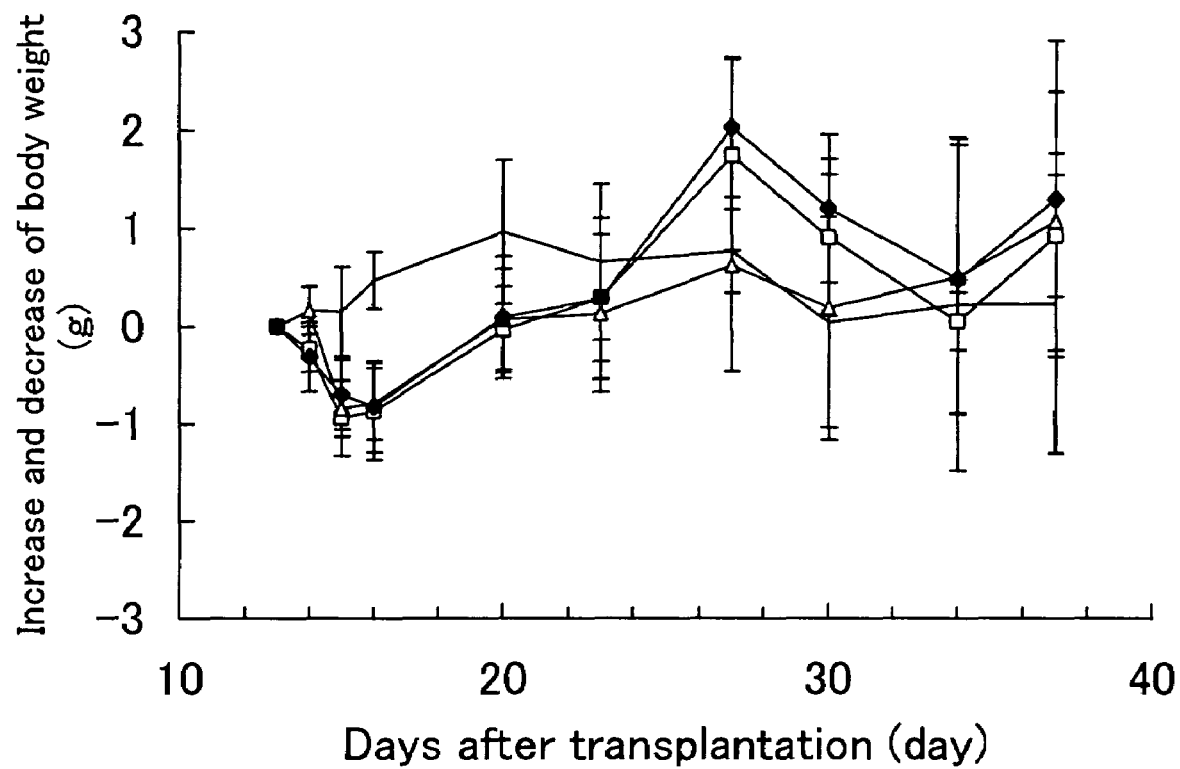
FIG. 10 shows a reducing effect of the body weight as a side effect when 0.8 times of the maximum tolerated dose of amrubicin hydrochloride and 0.8 times of the maximum tolerated dose of vinorelbine are used in combination. Line denotes a vehicle group, □ denotes an amrubicin hydrochloride alone administration group, Δ denotes a vinorelbine alone administration group and ♦ denotes a combined administration group.
Figure 11:
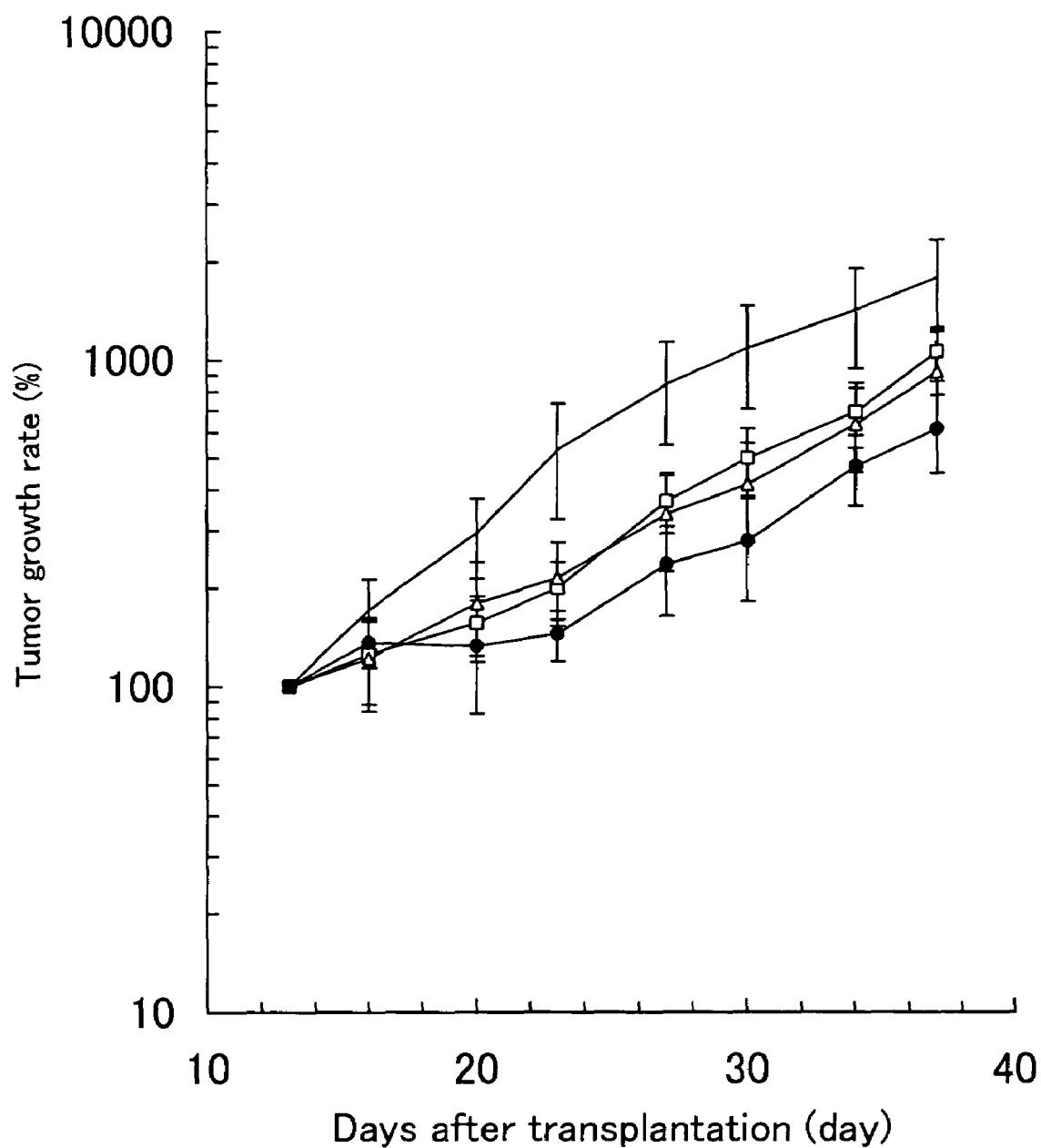
FIG. 11 shows an inhibitory effect of growth of squamous cell lung carcinoma cell when 1.0 time of the maximum tolerated dose of amrubicin hydrochloride and 1.0 time of the maximum tolerated dose of vinorelbine are used in combination. Line denotes a vehicle group, □ denotes an amrubicin hydrochloride alone administration group, Δ denotes a vinorelbine alone administration group and ● denotes a combined administration group.
Figure 12:
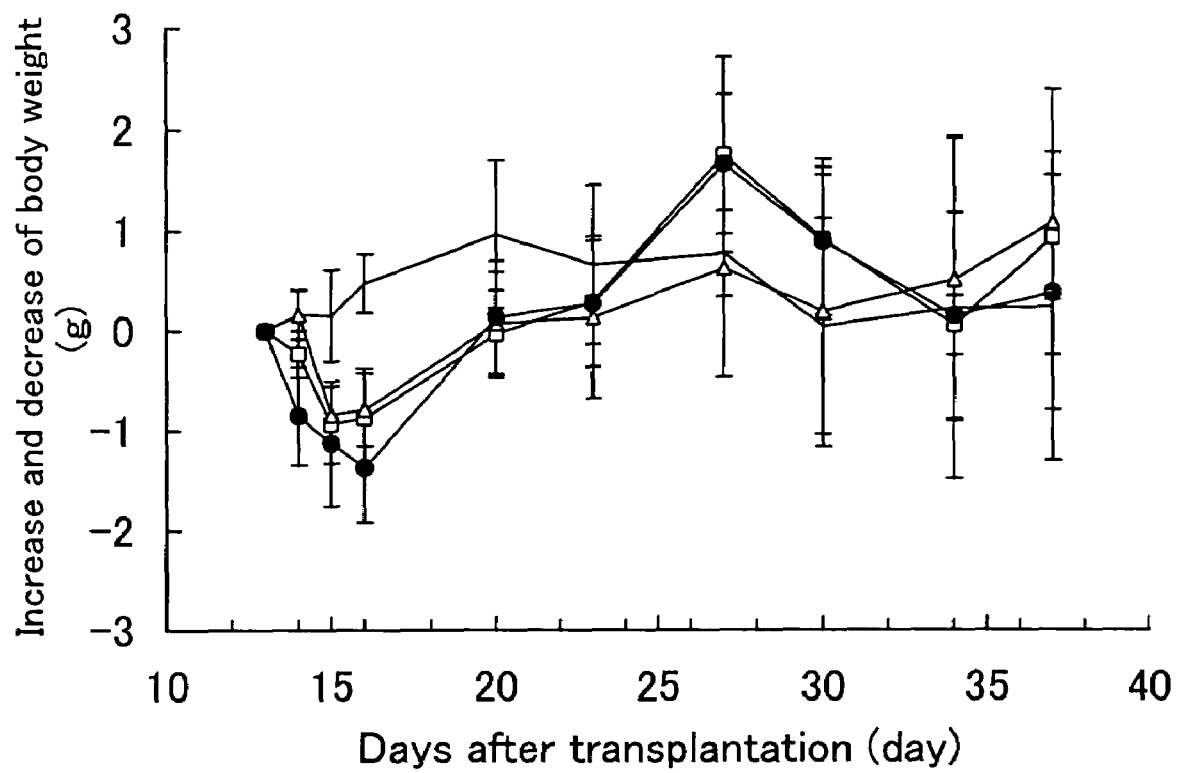
FIG. 12 shows a reducing effect of the body weight as a side effect when 1.0 time of the maximum tolerated dose of amrubicin hydrochloride and 1.0 time of the maximum tolerated dose of vinorelbine are used in combination. Line denotes a vehicle group, □ denotes an amrubicin hydrochloride alone administration group, Δ denotes a vinorelbine alone administration group and ● denotes a combined administration group.
Figure 13:
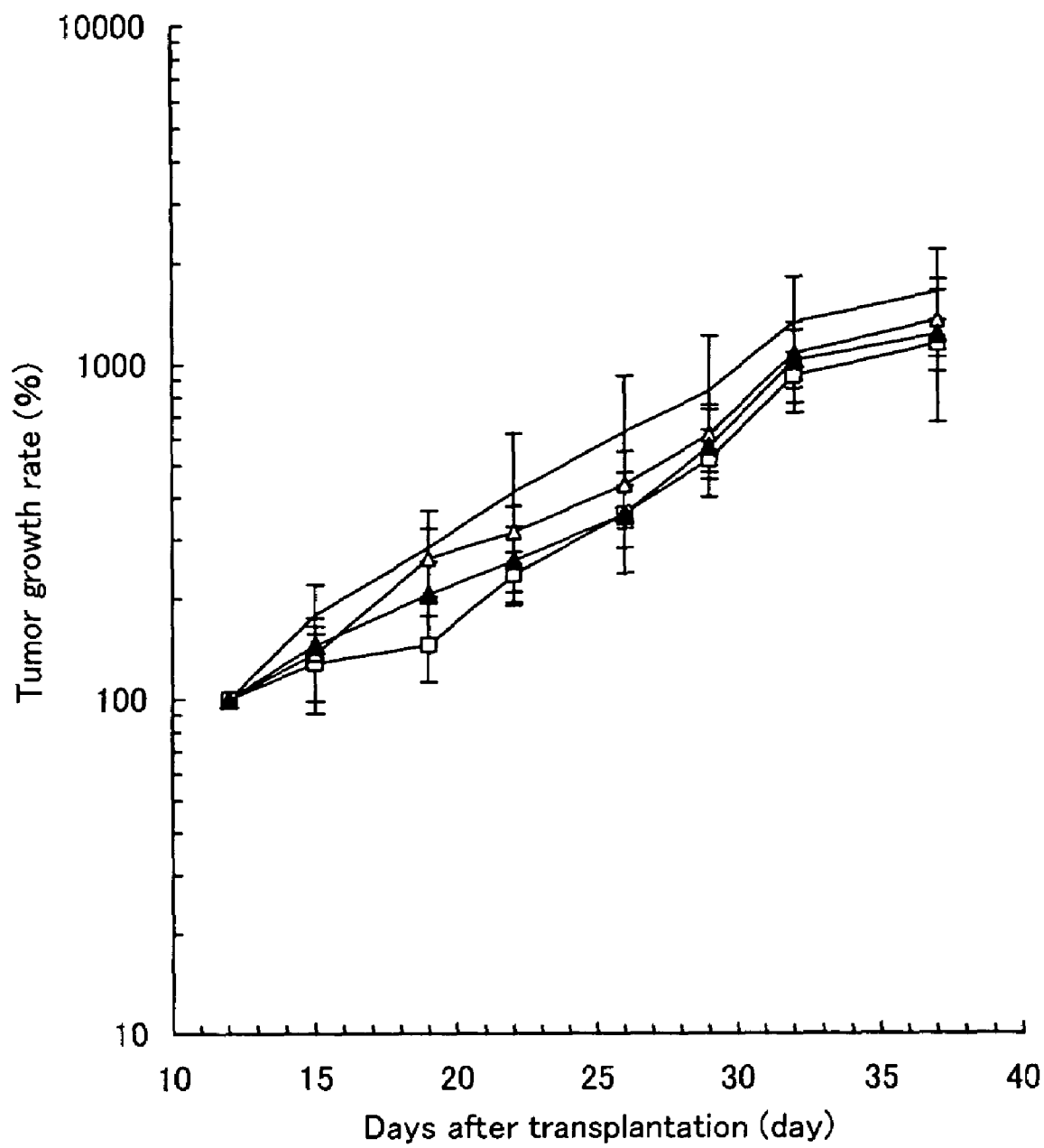
FIG. 13 shows an inhibitory effect of growth of squamous cell lung carcinoma cell when 0.5 times of the maximum tolerated dose of amrubicin hydrochloride and 0.5 times of the maximum tolerated dose of gemcitabine are used in combination. Line denotes a vehicle group, □ denotes an amrubicin hydrochloride alone administration group, Δ denotes a gemcitabine alone administration group and ▲ denotes a combined administration group.
Figure 14:
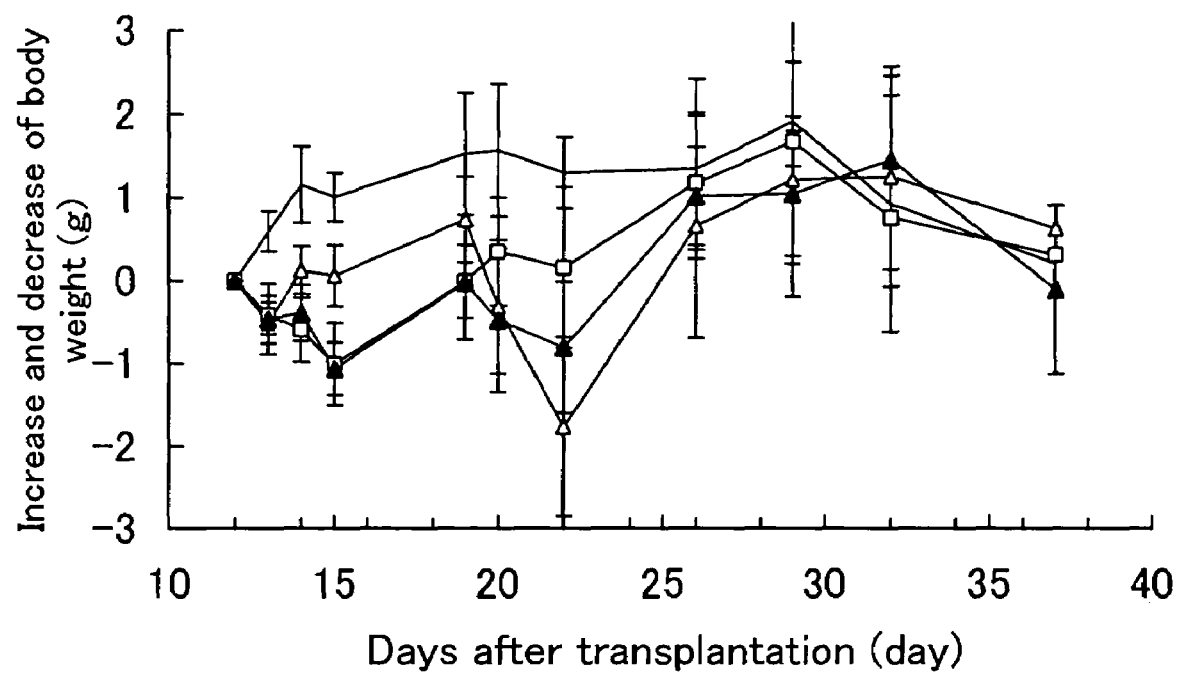
FIG. 14 shows a reducing effect of the body weight as a side effect when 0.5 times of the maximum tolerated dose of amrubicin hydrochloride and 0.5 times of the maximum tolerated dose of gemcitabine are used in combination. Line denotes a vehicle group, □ denotes an amrubicin hydrochloride alone administration group, Δ denotes a gemcitabine alone administration group and ▲ denotes a combined administration group.
Figure 15:
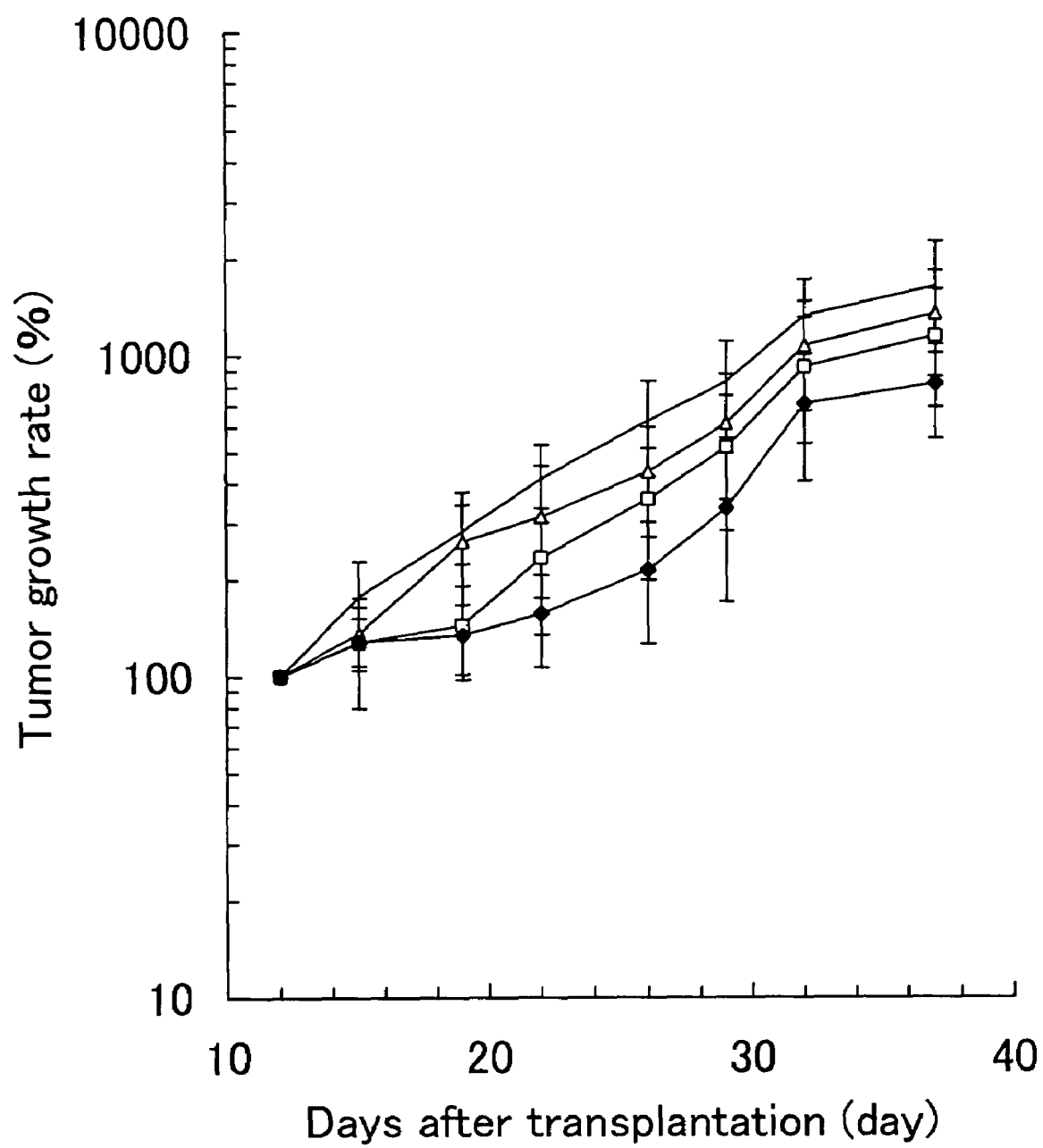
FIG. 15 shows an inhibitory effect of growth of squamous cell lung carcinoma cell when 0.8 times of the maximum tolerated dose of amrubicin hydrochloride and 0.8 times of the maximum tolerated dose of gemcitabine are used in combination. Line denotes a vehicle group, □ denotes an amrubicin hydrochloride alone administration group, Δ denotes a gemcitabine alone administration group and ♦ denotes a combined administration group.
Figure 16:
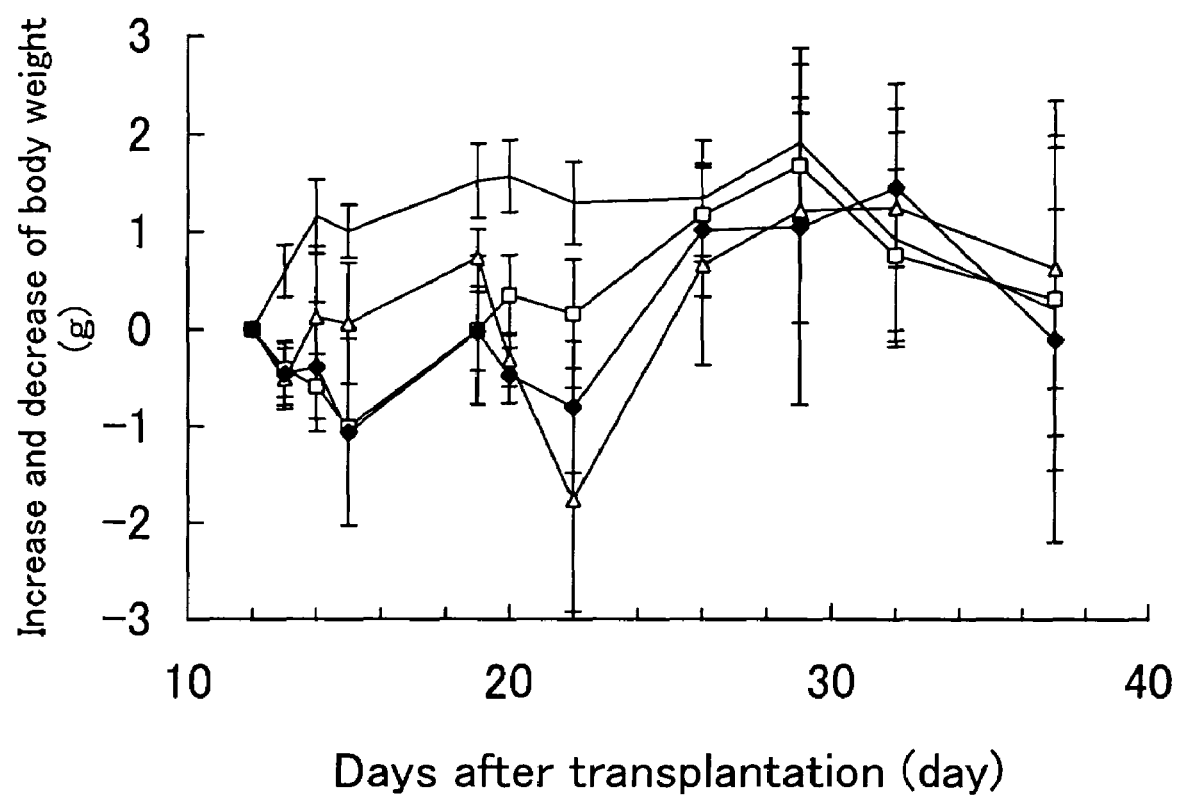
FIG. 16 shows a reducing effect of the body weight as a side effect when 0.8 times of the maximum tolerated dose of amrubicin hydrochloride and 0.8 times of the maximum tolerated dose of gemcitabine are used in combination. Line denotes a vehicle group, □ denotes an amrubicin hydrochloride alone administration group, Δ denotes a gemcitabine alone administration group and ♦ denotes a combined administration group.
Figure 17:
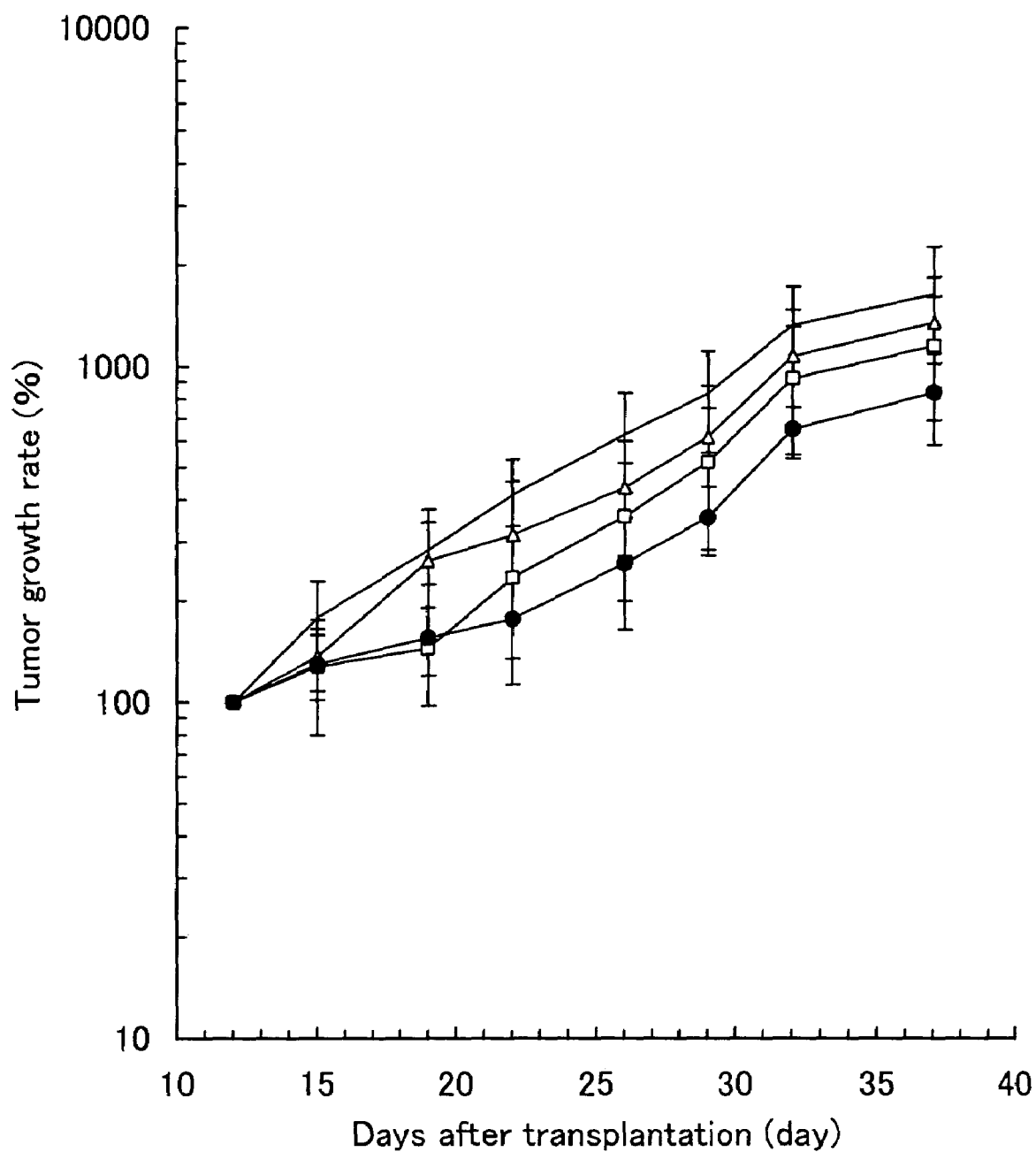
FIG. 17 shows an inhibitory effect of growth of squamous cell lung carcinoma cell when 1.0 time of the maximum tolerated dose of amrubicin hydrochloride and 1.0 time of the maximum tolerated dose of gemcitabine are used in combination. Line denotes a vehicle group, □ denotes an amrubicin hydrochloride alone administration group, Δ denotes a gemcitabine alone administration group and ● denotes a combined administration group.
Figure 18:
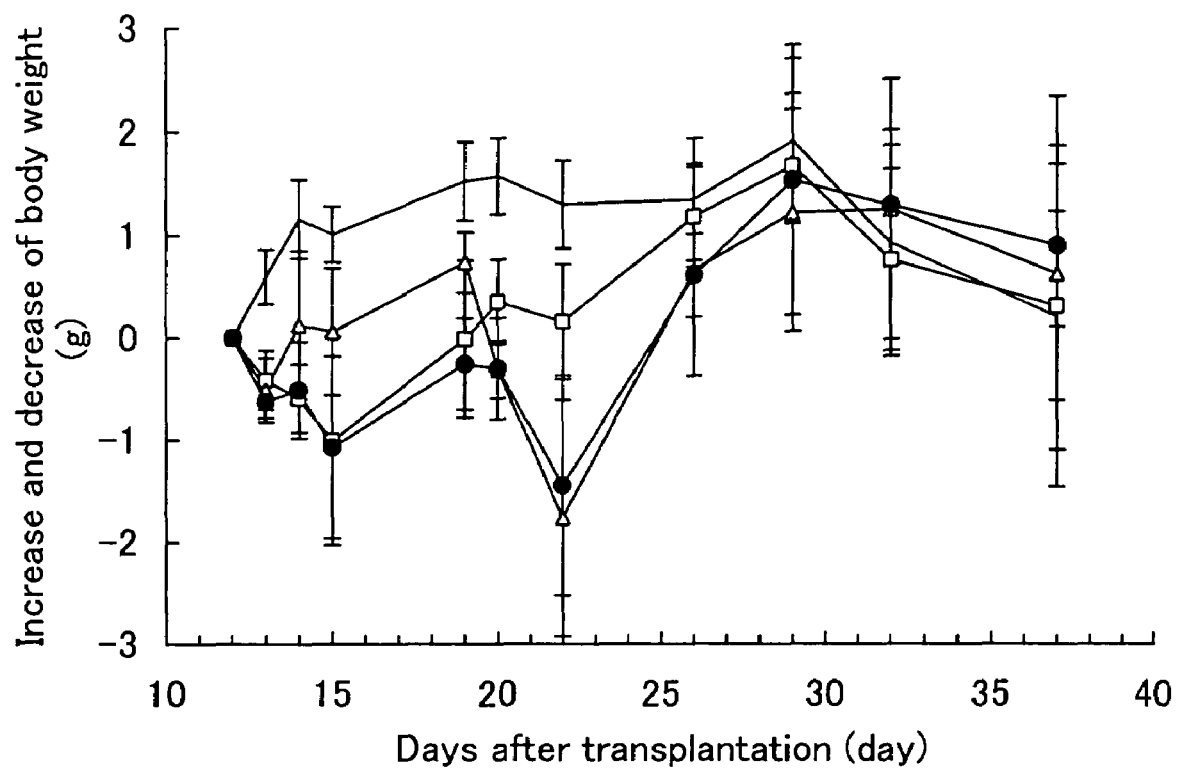
FIG. 18 shows a reducing effect of the body weight as a side effect when 1.0 time of the maximum tolerated dose of amrubicin hydrochloride and 1.0 time of the maximum tolerated dose of gemcitabine are used in combination. Line denotes a vehicle group, □ denotes an amrubicin hydrochloride alone administration group, Δ denotes a gemcitabine alone administration group and ● denotes a combined administration group.
Figure 19:
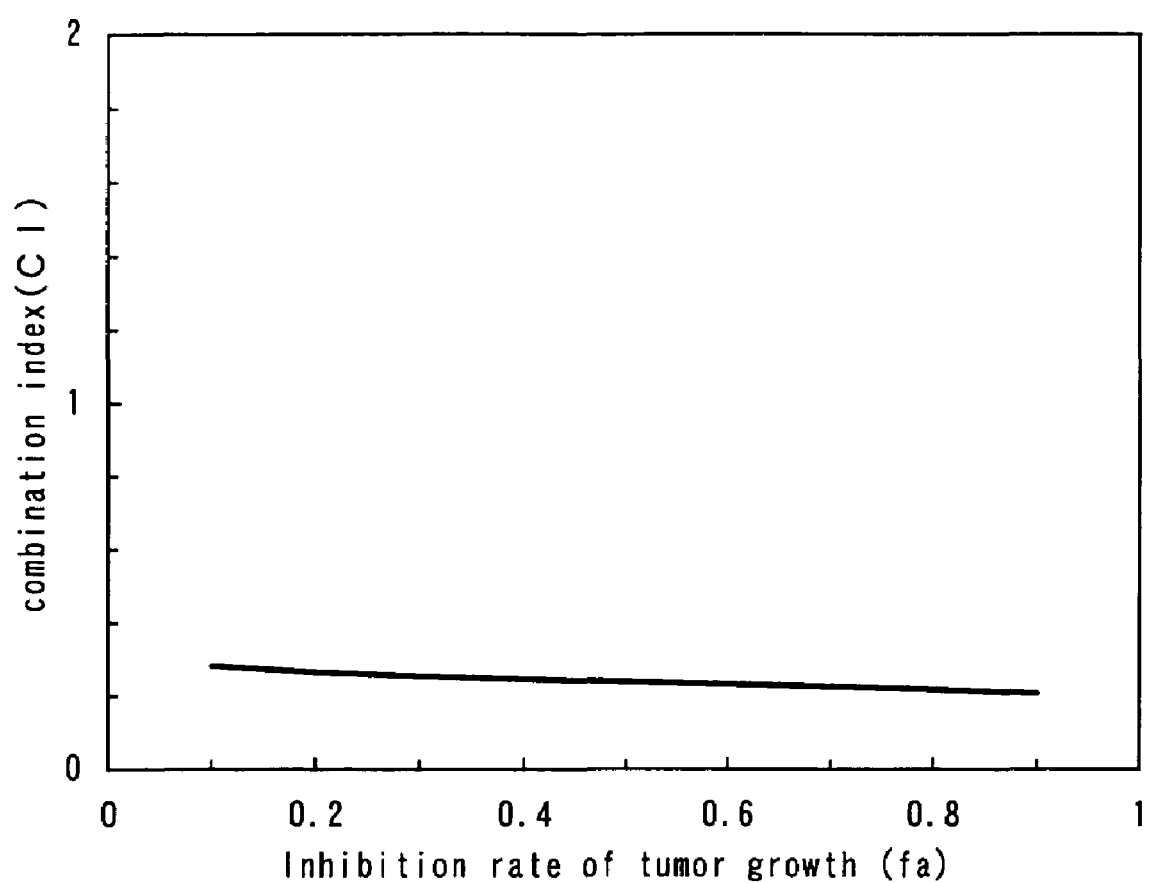
FIG. 19 shows in vitro effects by combination of amrubicinol hydrochloride and irinotecan. The CI values are plotted from 0.1 to 0.9 by the fa value, which shows a growth inhibition rate, on a horizontal axis and CI (combination index) value on a vertical axis.

According to the invention, medicament for treating lung cancer combined amrubicin hydrochloride with another medicament for treating lung cancer useful in the treatment of a subject of lung cancer is provided. By the combined use with the other medicament for treating lung cancer, the antitumor therapeutic effect of amrubicin hydrochloride can be improved and cancer therapy with reduced side effects of said medicament for treating lung cancer becomes possible.

The invention claimed is:

1. A method for treating a lung cancer which comprises administering to a patient in need thereof an effective amount of amrubicin or a pharmaceutically acceptable salt thereof and a second medicament for treating lung cancer, said second medicament being selected from the group consisting of irinotecan, vinorelbine and gemcitabine.

2. The method for treating lung cancer as described in claim 1, wherein the lung cancer is small cell lung cancer, lung adenocarcinoma, squamous cell lung carcinoma or large cell lung carcinoma.

3. The method for treating lung cancer as described in claim 1, wherein the lung cancer is small cell lung cancer or squamous cell lung carcinoma.

4. The method for treating lung cancer as described in claim 1, wherein the amrubicin or a pharmaceutically acceptable salt thereof is amrubicin hydrochloride.

5. The method for treating lung cancer as described in claim 1, wherein the second medicament for treating lung cancer is irinotecan.

6. The method for treating lung cancer as described in claim 1, wherein amrubicin or a pharmaceutically accept able salt thereof is administered simultaneously with, or sequentially with the other medicament for treating lung cancer.

7. The method for treating lung cancer as described in claim 1, wherein about 60 to about 150 mg/m$^2$ of amrubicin or a pharmaceutically acceptable salt thereof is administered in a single dose or in 2 to 5 divided doses.

8. The method for treating lung cancer as described in claim 7, wherein about 80 to about 130 mg/m$^2$ of amrubicin or a pharmaceutically acceptable salt thereof is administered in a single dose.

9. The method for treating lung cancer as described in claim 7, wherein about 110 to about 130 mg/m$^2$ of amrubicin or a pharmaceutically acceptable salt thereof is administered in a single dose.

10. The method for treating lung cancer as described in claim 7, wherein about 25 to about 50 mg/m$^2$ of amrubicin or a pharmaceutically acceptable salt thereof is administered once a day for 3 days.

11. The method for treating lung cancer as described in claim 7, wherein about 30 to about 45 mg/m$^2$ of amrubicin or a pharmaceutically acceptable salt thereof is administered once a day for 3 days.

12. The method for treating lung cancer as described in claim 7, wherein about 35 to about 45 mg/m$^2$ of amrubicin or a pharmaceutically acceptable salt thereof is administered once a day for 3 days.

13. The method for treating lung cancer as described in any of claims 10 to 12, wherein amrubicin or a pharmaceutically acceptable salt thereof is administered for continuous 3 days.

14. The method for treating lung cancer as described in claim 1, wherein the second medicament for treating lung cancer is administered in a combined use of about 0.4 times to about 1.0 time of the maximum tolerated dose or 0.4 times to about 1.0 time of the maximum administered dose.

15. The method for treating lung cancer as described in claim 1, in which the patient is one having failed to continue receiving the treatment with the second medicament for treating lung cancer because of side effects, and wherein said second medicament is administered in an amount that will cause reduced side effect.

16. A kit for treating lung cancer comprising
(a) a first composition comprising amrubicin or a pharmaceutically acceptable salt thereof as an active ingredient and;
(b) a second composition comprising another medicament for treating lung cancer as an active ingredient, wherein the other medicament for treating lung cancer is selected from the group consisting of irinotecan, vinorelbine and gemcitabine.

* * * * *